(12) United States Patent (10) Patent No.: US 8,404,658 B2
Hajjar et al. (45) Date of Patent: Mar. 26, 2013

(54) RNA INTERFERENCE FOR THE TREATMENT OF HEART FAILURE

(75) Inventors: Roger J. Hajjar, New York, NY (US); Wolfgang Ch. Poller, Falkensee (DE); Henry Fechner, Luckau (DE)

(73) Assignee: NanoCor Therapeutics, Inc., Chapel Hill, NC (US)

( * ) Notice: Subject to any disclaimer, the term of this patent is extended or adjusted under 35 U.S.C. 154(b) by 0 days.

(21) Appl. No.: 12/811,306

(22) PCT Filed: Dec. 23, 2008

(86) PCT No.: PCT/US2008/088248
§ 371 (c)(1), (2), (4) Date: Dec. 15, 2010

(87) PCT Pub. No.: WO2009/088786
PCT Pub. Date: Jul. 16, 2009

(65) Prior Publication Data
US 2011/0098338 A1 Apr. 28, 2011

Related U.S. Application Data

(60) Provisional application No. 61/018,326, filed on Dec. 31, 2007.

(51) Int. Cl.
*C12N 15/11* (2006.01)
(52) U.S. Cl. .................................. 514/44 A
(58) Field of Classification Search .................. 514/44 A
See application file for complete search history.

(56) References Cited

U.S. PATENT DOCUMENTS

| 2005/0019927 | A1 | 1/2005 | Hildinger et al. |
| 2006/0148742 | A1 | 7/2006 | Kaye et al. |
| 2006/0198825 | A1 | 9/2006 | Kaemmerer et al. |

FOREIGN PATENT DOCUMENTS

| WO | WO 2006/084207 A2 | 8/2006 |
| WO | WO 2007/028969 A2 | 3/2007 |
| WO | WO-2008080985 A1 | 7/2008 |

OTHER PUBLICATIONS

He et al. (Acta Pharmacologica Sinica, Jul. 2003, 24(7):637-640).*
EPO Form 1507S, May 23, 2011, Extended European Search Report for 08869943.4.
Form PCT/ISA/210, Mar. 26, 2009, ISR for PCT/US2008/088248.
Form PCT/IB/373, Jul. 6, 2010, Preliminary Report on Patentability for PCT/US2008/088248.
Xiaochun Lu et al., "Knock down Phospholamban to Improve Heart Function by AAV-Mediated shRNA", Molecular Therapy, vol. 13, No. suppl. 1, 238, May 2006, pp. S91-S92, XP002636271.
Andino Lourdes M e tl., "AAV-mediated knockdown of phospholamban leads to improved contractility and calcium handling in cardiomyocytes"., The Journal of Gene Medicine, Feb. 2008, LNKD—PUBMED: 18064719, vol. 10, No. 2, Dec. 7, 2007, pp. 132-142, XP002636188, ISSN: 1099-498X.
Fechner H et al., "Highly efficient and specific modulation of cardiac calcium homeostasis by adenovector-derived short haripin RNA targeting phospholamban", Gene Therapy, Macmillan Press Ltd., Basingstoke, GB, vol. 14, No. 3, Oct. 5, 2006, pp. 211-218, XP002430901.
Poller Wolfgang et al., "Chronic Cardiac-Targeted RNA Interference for the Treatment of Severe Heart Failure Restores Cardiac Function and Reduces Pathological Hypertrophy", Circulation, vol. 118, No. 18, Suppl. 2, Oct. 2008, p. S488, XP002636189.
Watanabe A et al., "Phospholamban ablation by RNA interference increases Ca<2+>uptake into rat cardiac myocyte sarcoplasmic reticulum", Journal of Molecular and Cellular Cardiology, Academic Press, GB, vol. 37, No. 3, Sep. 1, 2004, pp. 691-698, XP004537253.
Inagaki et al., "Robust systemic transduction with AAV9 vectors in mice: efficient global cardiac gene transfer superior to that of AAV8", Molecular Therapy, Academic Press, San Diego, CA, US, vol. 14, No. 1, Jul. 1, 2006, pp. 45-53, XP005560370.
Pacak Christina A et al., "Recombinant adeno-associated virus serotype 9 leads to preferential cardiac transduction in vivo"., Circulation Research Aug 18, 2006 LNKD—PUBMED: 16873720, vol. 99, No. 4, Aug. 18, 2006, pp. E3-E9, XP002636190.
Vandendriessche T et al., "Efficacy and safety of adeno-associated viral vectors based on serotype 8 and 9 vs. lentiviral vectors for hemophilia B gene therapy". Journal of Thrombosis and Haemostasis: JTH Jan. 2007 LNKD—PUBMED:17002653, vol. 5, No. 1, Jan. 2007, pp. 16-24, XP002636191.

* cited by examiner

*Primary Examiner* — Jon E Angell
(74) *Attorney, Agent, or Firm* — Edwards Wildman Palmer LLP; Peter C. Lauro, Esq.; Melissa Hunter-Ensor, Esq.

(57) ABSTRACT

The present invention relates to targeted RNAi for the treatment of heart failure by modulating defective cardiac $Ca^{2+}$ homeostasis via decreasing expression or activity of phospholamban (PLB) using adeno-associated virus (AAV) transfection of cardiomyocytes. Methods for decreasing ventricular arrhythmias, as well as methods for overall improvement of survival from heart failure in subjects are also disclosed. Further, the present invention provides methods which can be used to diagnose susceptibility to treatment by RNAi, and includes pharmaceutical compositions, kits and vectors including an RNAi sequence.

11 Claims, 18 Drawing Sheets

‡: p<0.05 for AAV9-shGFP vs. AAV9-shPLB
¶: p<0.05 for AdV-shGFP vs. AdV-shPLB

‡: p<0.05 for AAV9-shGFP vs. AAV9-shPLB
¶: p<0.05 for AdV-shGFP vs. AdV-shPLB

‡: p<0.05 for AAV9-shGFP vs. AAV9-shPLB
¶: p<0.05 for AdV-shGFP vs. AdV-shPLB

‡: p<0.05 for AAV9-shGFP vs. AAV9-shPLB
¶: p<0.05 for AdV-shGFP vs. AdV-shPLB

RNA INTERFERENCE FOR THE TREATMENT OF HEART FAILURE

CROSS REFERENCE TO RELATED APPLICATIONS

This application is a 35 USC §371 National Stage application of International Application No. PCT/US2008/088248 filed Dec. 23, 2008, now pending; which claims the benefit under 35 USC §119(e) to U.S. application Ser. No. 61/018,326 filed Dec. 31, 2007, now abandoned. The disclosure of each of the prior applications is considered part of and is incorporated by reference in the disclosure of this application.

GRANT INFORMATION

This invention was made with government support under Grant Nos. R01 HL078691, HL071763, HL080498, HL083156 and K01 HL076659 awarded by the National Institutes of Health. The government has certain rights in the invention.

BACKGROUND OF THE INVENTION

1. Field of the Invention

The invention relates generally to methods of treating heart disease and, more specifically, to a method of using RNAi to reduce phospholamban (PLB) for the treatment of chronic heart failure, including delivery by adeno-associated virus (AAV), a targeting AAV9 vector, and a method of diagnosing susceptibility to treatment by RNAi for chronic heart failure.

2. Background Information

Heart failure currently affects more than two million Americans and its economic and human toll will continue to increase as the population ages. Congestive heart failure is the most common inpatient diagnosis for patients 65 years old and older, with more than 400,000 new cases reported each year. The prognosis is poor, with 60% mortality within 5 years, and 23-52% of deaths attributable to fatal arrhythmias (sudden cardiac death; SCD).

Heart failure is an inability to match cardiac output to physiological demand. Heart failure is therefore not a specific disease, but a syndrome that represents the end-point of most cardiac diseases, including ischemic heart disease, cardiomyopathies (dilative, restrictive, or hypertrophic), valvular heart diseases and chronic hypertension and diabetes. In addition, the symptoms of heart failure can also present acutely (i.e., acute heart failure, or cardiogenic shock) in instances as acute myocardial infarction, post cardiac surgery (stunning, hybernation) or post re-vascularization therapy (i.e. reperfusion injury, post thrombolysis, percutaneous transluminal coronary angioplasty or coronary artery by-pass grafting).

Depressed contractility is a central feature of congestive heart failure, and the sarcoplasmic reticulum (SR), which stores calcium in cardiomyocytes, plays a key role in cardiac contractility as well as in the coupling of excitation and contraction. The development of contractile force depends on the amount of $Ca^{2+}$ accumulated in the SR. An increase in abundance of the sarcoplasmic reticulum calcium ATPase (SERCAa) or increase in the phosphorylation of phospholamban (PLB) and/or decrease in PLB abundance may contribute to an increase in $Ca^{2+}$ uptake by the SR, thereby enhancing the contractility of cardiomyocytes.

PLB is a 53 amino acid, muscle-specific phosphoprotein. Dephosphorylated PLB binds with SERCA2a and regulates the amount of calcium that enters into the SR in cardiac muscle. When phosphorylated by protein kinase A, PLB inhibition of SERCA2a is relived, increasing calcium flux into the SR and enhancing contractility of the muscle.

Myocardial gene therapy can be used for the treatment of a number of cardiovascular diseases, including ischemic cardiomyopathies, congestive heart failure, and malignant arrhythmias. A useful vector for myocardial gene delivery would allow efficient and stable transduction of cardiomyocytes with a variety of transgenes after either direct intramyocardial injection or infusion into the coronary arteries or sinuses. For example, plasmid DNA vectors injected directly into the left ventricular myocardium have been expressed for 6 months by cardiomyocytes adjacent to the area of injection. However, the therapeutic usefulness of this approach has been limited by the low efficiency of cardiomyocyte transduction (0.1% to 1.0% of cardiomyocytes in the area of injection).

Both intramyocardial injection and intracoronary infusion of replication-defective adenovirus (RDAd) vectors have been used to efficiently transduce cardiomyocytes in rodents, rabbits, and pigs in vivo. However, the feasibility of adenovirus-mediated gene transfer has been limited by immune responses to viral and foreign transgene proteins, which cause significant myocardial inflammation, elimination of virus-transduced cells within 30 days of infection, and thereby result in transient recombinant gene expression in immunocompetent hosts.

SUMMARY OF THE INVENTION

The present invention relates to targeted RNAi for the treatment of severe heart failure by modulating defective cardiac $Ca^{2+}$ homeostasis via decreasing expression of phospholamban (PLB) using adeno-associated virus (AAV) transfection of cardiomyocytes. The method also relates to decreasing ventricular arrhythmias, as well as to overall improvement in survival from heart failure in subjects using the disclosed methods. Further, the present invention provides methods which can be used to diagnose susceptibility to treatment by RNAi, and includes pharmaceutical compositions, kits and vectors consisting essentially of an RNAi which reduces PLB activity.

As such, the invention provides a method of treating heart failure in a subject. The method includes administering to a subject in need thereof a vector including an RNAi expression cassette, where the cassette comprises an RNAi sequence whose expression product decreases phospholamban (PLB) activity, in an amount effective to treat heart failure in the subject and improve systolic function in the subject as compared to prior to administration of the vector. In one embodiment, the vector is a virion. In another embodiment, the vector is a plasmid. In another embodiment, the virion is a parvovirus. In another embodiment, the parvovirus is an adeno-associated virus (AAV), including AAV serotype 9. In yet another embodiment, the RNAi expression cassette includes a nucleotide sequence as set forth in SEQ ID NO:1. In a related embodiment, SEQ ID NO:1 is flanked by AAV terminal repeats. In another embodiment, PLB gene expression is inhibited by at least 10%. In another embodiment, the RNAi sequence includes a target sequence as set forth in SEQ ID NO:2. As such, the RNAi expression cassette encodes at least one RNA including a first nucleotide sequence that hybridizes under stringent conditions to a nucleotide sequence of the PLB gene, and a second nucleotide sequence which is a complementary inverted repeat of the first nucleotide sequence and hybridizes to the first nucleotide sequence to form a hairpin structure. In one embodiment, the two nucleotide sequences are joined by an RNA loop structure. In another embodiment, the subject is a mammal, such as a human.

The invention further provides a pharmaceutical composition including a recombinant adeno-associated virus (AAV) vector and a pharmaceutically acceptable carrier, where the vector comprises an RNAi expression cassette whose RNA expression product leads to a decrease in expression and/or activity of phospholamban (PLB). In one embodiment, the RNA expression product of the RNAi expression cassette includes a nucleotide sequence that hybridizes under stringent conditions to a nucleotide sequence of the PLB gene mRNA, where stringent conditions include, but are not limited to, hybridization at 42° C. in a solution comprising 50% formamide, 5×SSC, and 1% SDS and washing at 65° C. in a solution comprising 0.2×SSC and 0.1% SDS. In another embodiment, the RNAi expression cassette includes a nucleotide sequence as set forth in SEQ ID NO:1. In another embodiment, the RNA expression product includes a target sequence as set forth in SEQ ID NO:2. In another embodiment, the composition is suitable for intravenous administration, intra-arterial administration, intraventricular administration, or heart valve perfusion.

The invention further provides, an adenovirus associated virus (AAV) vector including at least one AAV terminal repeat, where the vector comprises an RNAi expression cassette, whose RNAi expression product leads to a decrease in expression of phospholamban (PLB) mRNA or PLB activity. In embodiment, the RNA expression product of the RNAi expression cassette includes a nucleotide sequence that hybridizes under stringent conditions to a nucleotide sequence of the PLB gene mRNA. In another embodiment, the RNAi expression cassette includes a nucleotide sequence as set forth in SEQ ID NO:1. In another embodiment, the RNA expression product includes a target sequence as set forth in SEQ ID NO:2.

The invention further provides a method of increasing calcium uptake into the sarcoplasmic reticulum (SR). The method includes contacting a muscle tissue sample with an adeno-associated virus (AAV) vector, where the vector includes a polynucleotide sequence encoding an RNAi expression product thereby increasing calcium uptake in the SR and enhancing contractility of cardiomyocytes as compared to contractility prior to contact with the vector. In one embodiment, the RNAi includes a nucleotide sequence that hybridizes under stringent conditions to a nucleotide sequence of the PLB target gene mRNA. In another embodiment, the vector includes a nucleotide sequence as set forth in SEQ ID NO:1. In another embodiment, the RNAi includes a target sequence as set forth in SEQ ID NO: 2. In another embodiment, the RNA coding region of the RNAi expression cassette results in the down-regulation of the expression of the PLB gene. In another embodiment, the RNAi vector includes a sequence that is at least about 90% identical with the RNA coding region of the PLB target gene.

The invention further provides a kit including an adeno-associated virus (AAV) vector, where the vector comprises a polynucleotide sequence encoding an RNAi expression product which leads to a decrease in expression of phospholamban (PLB) mRNA or PLB activity, one or more buffers, instructions on using these components, and a container comprising these components. In embodiment, the RNAi includes a nucleotide sequence that hybridizes under stringent conditions to a nucleotide sequence of the PLB target gene mRNA transcript The invention further provides a method for diagnosing susceptibility of a subject to treatment by RNAi for chronic heart failure (HF) due to dysregulation of intracellular calcium in the subject. The method includes contacting a muscle tissue sample from a subject with an adeno-associated virus (AAV) vector, where the vector includes a polynucleotide sequence encoding an RNAi expression product which leads to a decrease in expression of phospholamban (PLB) mRNA or activity and determining the activity of a calcium ATPase pump (SERCA) in the tissue sample before and after contacting the muscle tissue sample with the AAV vector, where an increase in SERCA activity correlates with susceptibility of a subject to treatment by RNAi for HF.

The invention further provides a method of improving survival in a subject having chronic heart failure (HF). The method includes administering an adeno-associated virus (AAV) vector, where the vector includes a polynucleotide sequence encoding an RNAi expression product which leads to a decrease in expression of phospholamban (PLB) mRNA and a decrease in the amount of PLB protein in the cell, and where the RNAi includes a nucleotide sequence that hybridizes under stringent conditions to a nucleotide sequence of the PLB target gene mRNA. In one embodiment, the vector improves systolic function, thereby improving survival of the subject. In another embodiment, the AAV is serotype 9.

The invention further provides a method of reducing ventricular arrhythmias in a subject. The method includes administering a virion comprising a polynucleotide sequence encoding an RNAi expression product which leads to a decrease in expression of phospholamban (PLB) mRNA or PLB activity which improves ventricular function, thereby reducing ventricular arryhthmias in the subject. In one embodiment, the virion is AAV9.

BRIEF DESCRIPTION OF THE DRAWINGS

FIG. 2I is a pictorial diagram showing GFP expression in other organs one month after intravenous rAAV9-GFP injection. The left panels (RAAV9-GFP) are shown with primary GFP antibody, while the right panels (Cont) are shown without.

Echocardiography showed normalized fraction shortening (FS) after 3 months of rAAV-shPLB therapy, whereas FS improvement was also significant but less pronounced for AdV-shPLB. The maximal rate of pressure rise (+dP/dt) was improved compared to controls, also the systolic pressure (LVSP).

Figure 3A:
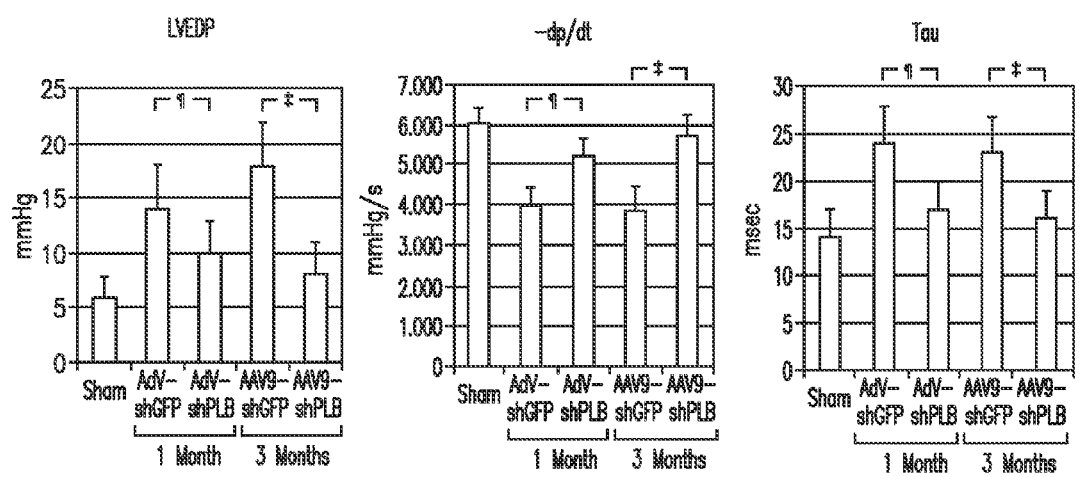
FIG. 3A is a series of graphical diagrams demonstrating the functional and morphological effects of RNAi therapy on HF. The influence of the RNAi treatments on hemodynamic parameters of diastolic LV function are summarized therein. The high LV filling pressure (LVEDP) in rats after TAB was significantly lowered by shPLB vectors (lanes 3,5) compared to shGFP controls (lanes 2,4). The maximal rate of pressure fall (−dP/dt) was significantly increased by shPLB treatment, also the isovolumetric relaxation time constant Tau. Values were restored to normal range (lane 1) after 3 months of rAAV-shPLB therapy (lane 5).
Figure 3B:
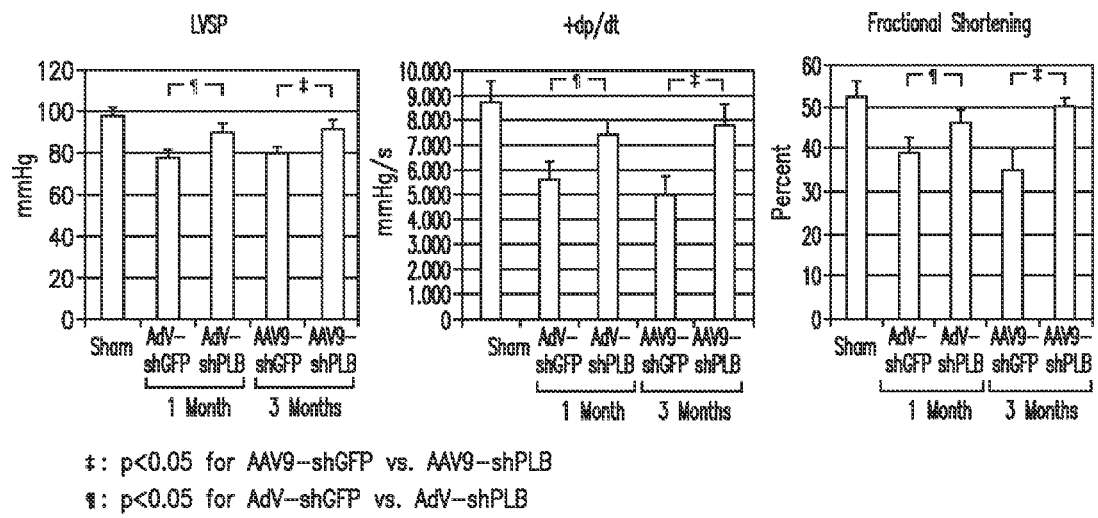
FIG. 3B is a series of graphical diagrams showing treatment effects on systolic LV function analogous to FIG. 3A.
Figure 3C:
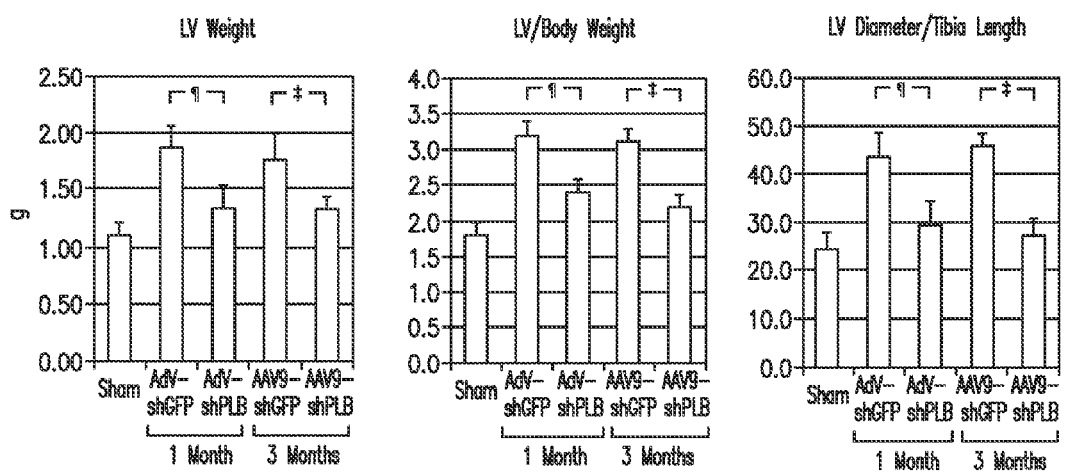

FIG. 3C is a series of graphical diagraphs showing post mortem morphometry shows marked LV hypertrophy induced by TAB (lanes 2,4) with LV weight and LV/body weight (LV/BW) ratio ~2/3 thirds above baseline (lane 1). The latter was reduced to within the normal range after 1 or 3 months of therapy with AdV-shPLB or rAAV9-shPLB (lanes 3,5). Cardiac hypertrophy was significantly reduced by both vector types.

Figure 3D:
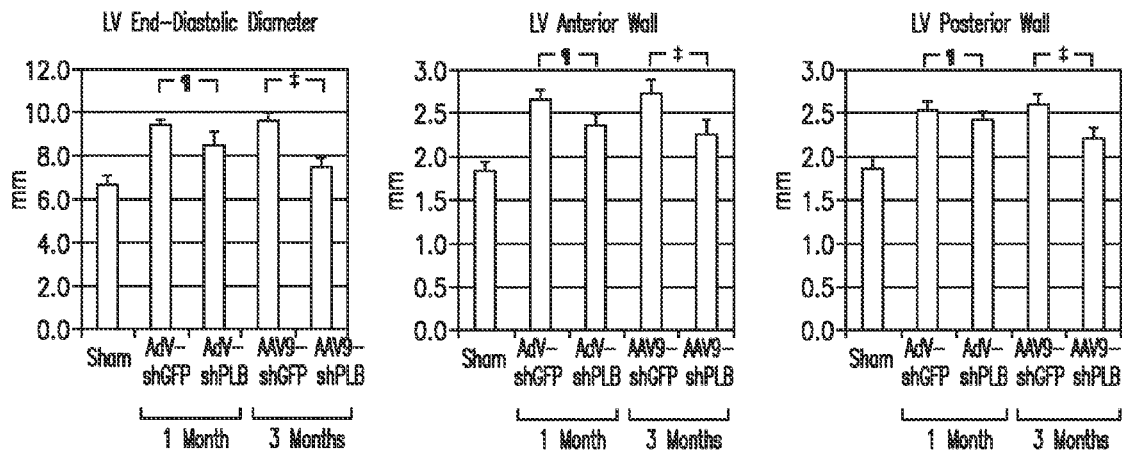

FIG. 3D is a series of graphical diagraphs summarizing the echocardiographic data of cardiac morphology, analogous to FIG. 3C, which corroborate the morphometric findings.

Figure 3E:
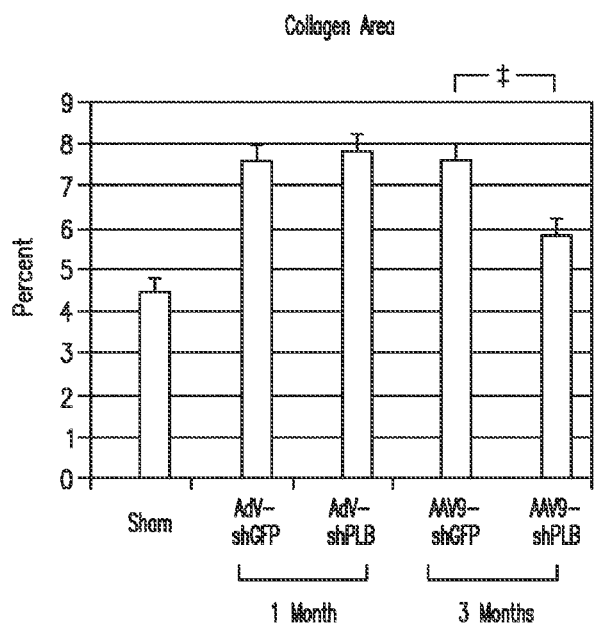

FIG. 3E is a graphical diagram showing cardiac collagen content in HF animals after RNAi therapy. rAAV9-shRNA treatment resulted in significantly reduced fibrosis at 3 months. The control vectors had no effect.

Figure 3F:
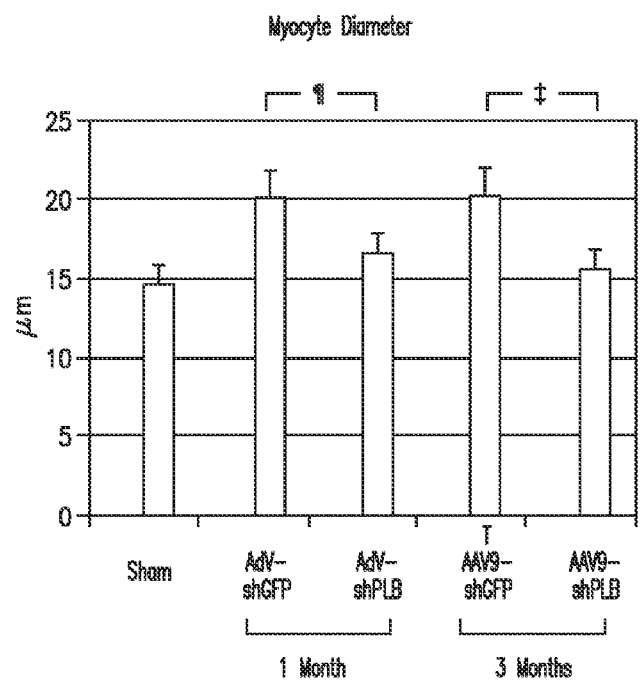

FIG. 3F is a graphical diagram showing that both treatment modes induced a significant decrease in cardiomyocyte diameters.

Figure 3G:
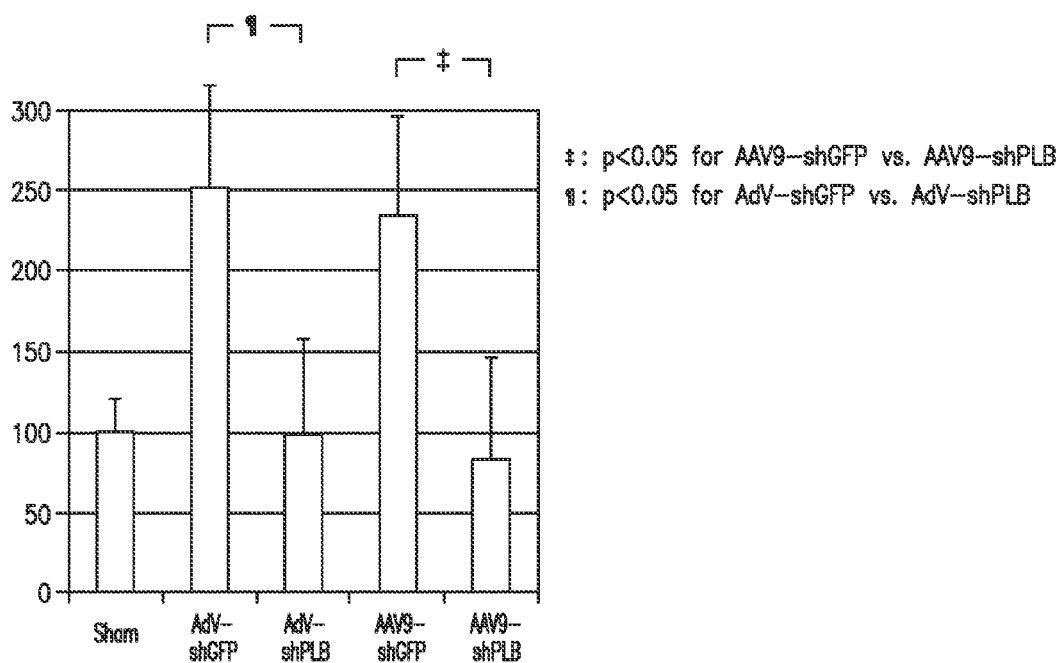

FIG. 3G is a graphical diagram showing cardiac BNP mRNA levels during RNAi treatment. ‡ denotes p<0.05 for AAV9-shGFP vs. AAV9-shPLB; ¶ denotes p<0.05 for AdV-shGFP vs. AdV-shPLB.

Figure 4A:
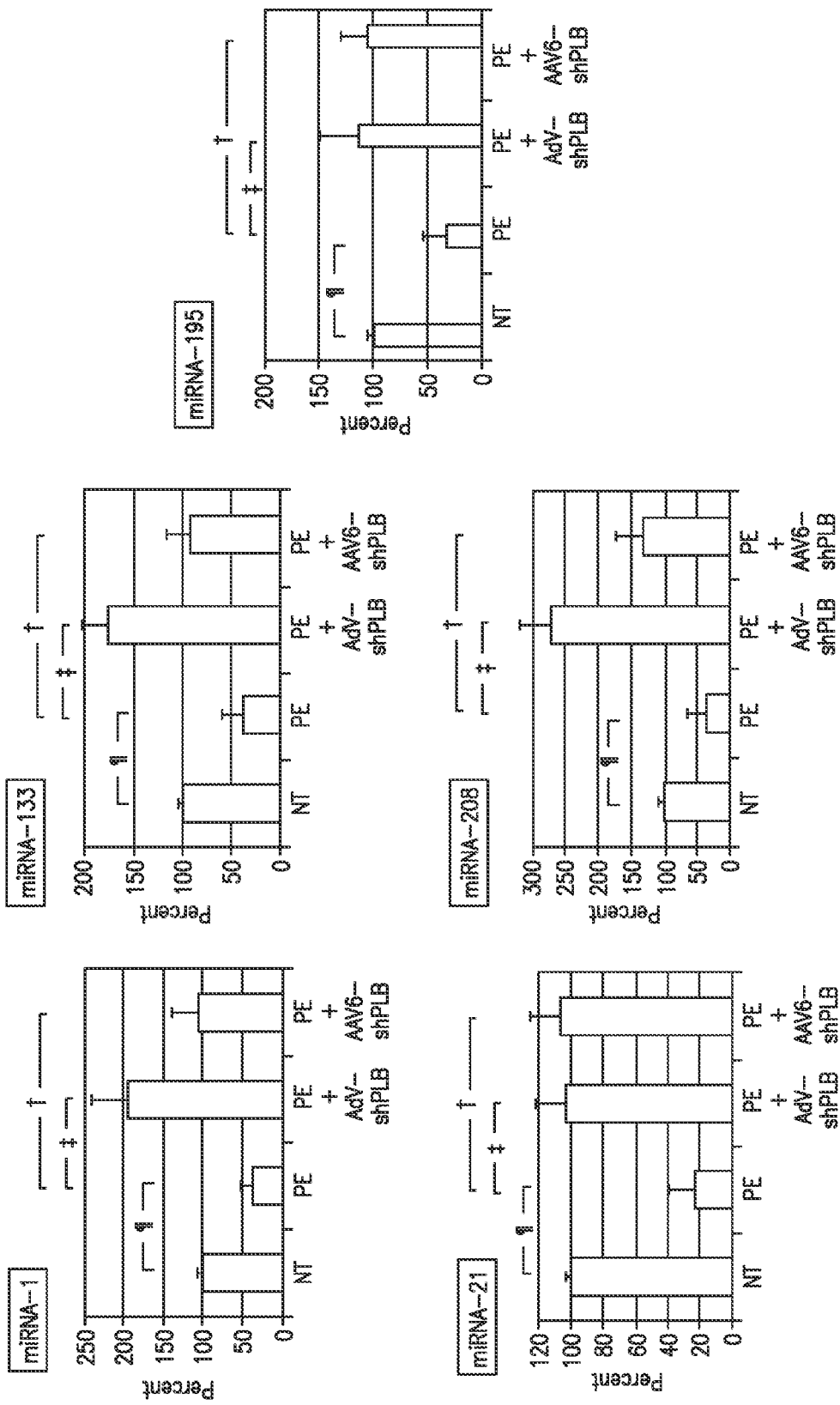

FIG. 4A is a series of graphical diagrams showing evaluation of cellular microRNAs during RNAi treatment. As shown, the cellular levels of five cardiac expressed microRNAs (miRs) were unchanged compared to untreated PNCMs during treatment with the vectors later used for in vivo therapy (AAV-shPLB, AAV-shGFP, AdV-shPLB), whereas vectors harboring a CMV promoter significantly altered those levels.

Figure 4B:
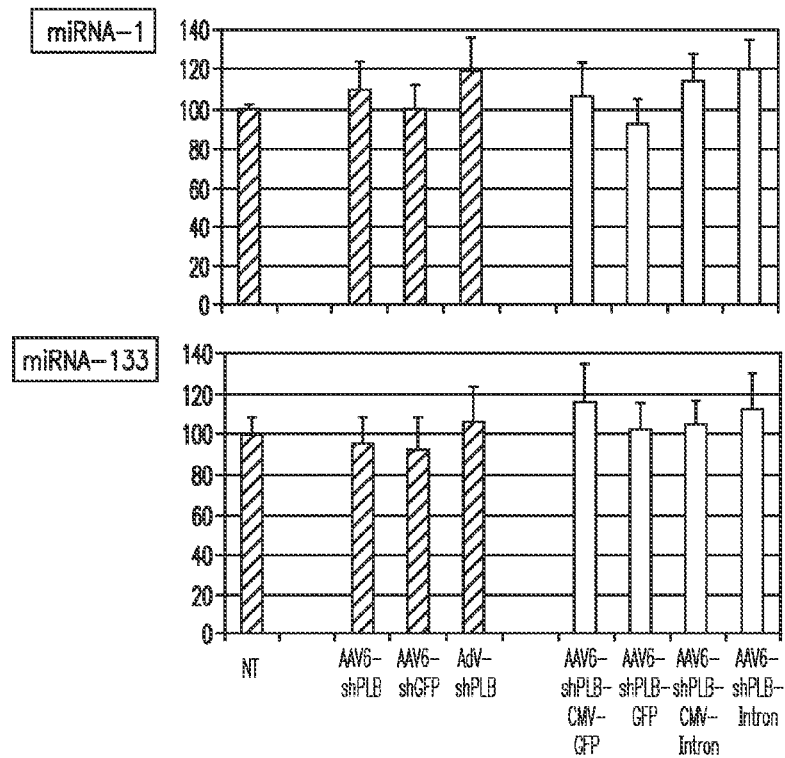

FIG. 4B is a series of graphical diagrams showing that, in contrast to the data of FIG. 4A obtained under standard PNCM culture conditions, cellular miRNA levels were significantly altered in the presence of hypertrophy-inducing drugs.

Figure 4C:
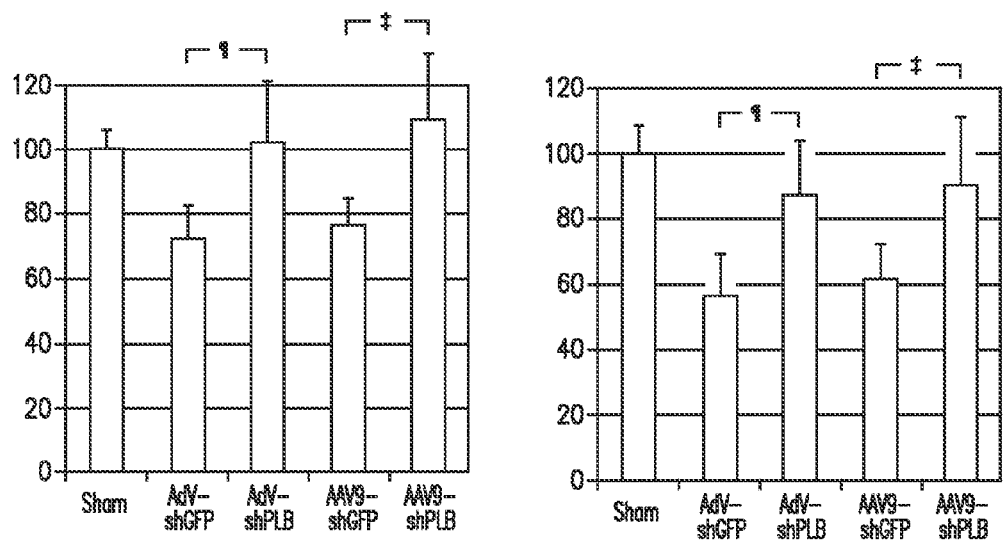

FIG. 4C is a series of graphical diagrams showing cardiac miRNA-1 and miRNA-133 levels during RNA1 therapy. ‡ denotes p<0.05 for AAV9-shGFP vs. AAV9-shPLB; ¶ denotes p<0.05 for AdV-shGFP vs. AdV-shPLB.

Figure 5A:
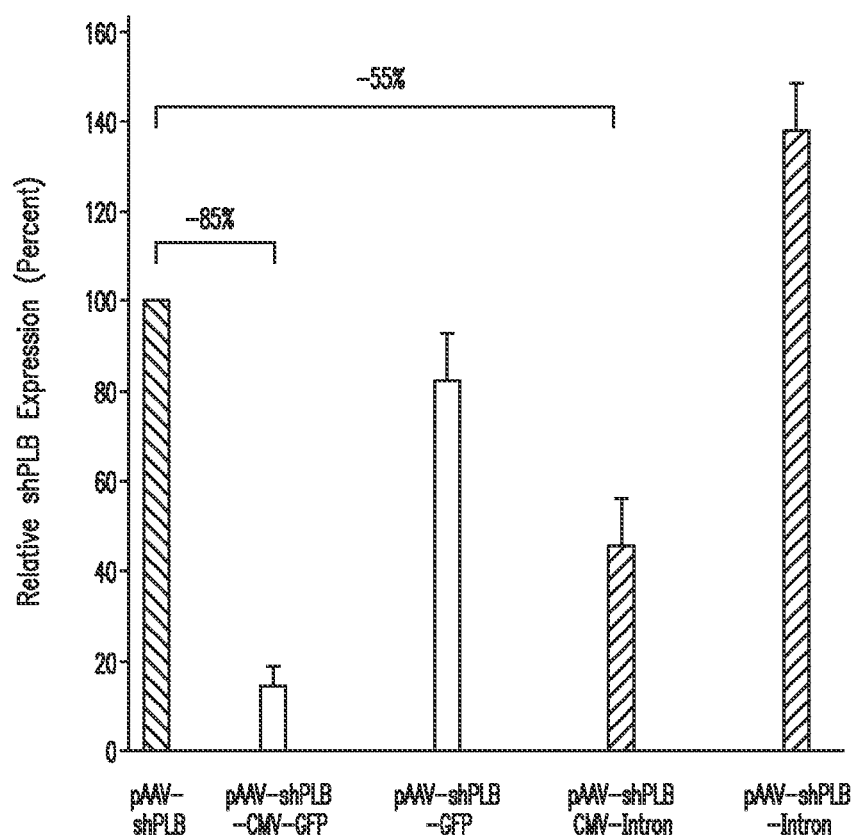

FIG. 5A is a graphical diagram showing the interference of CMV promoter with shRNA production. As shown, in addition to the different AAV vectors analyzed in FIGS. 1A and 1B, a direct comparison of vectors AAV-shPLB-CMV-GFP (with a functional GFP cassette) vs. AAV-shPLB-GFP (without a CMV promoter), and AAV-shPLB-CMV-β-intron vs AAV-shPLB-β-intron (without CMV).

Figure 5B:
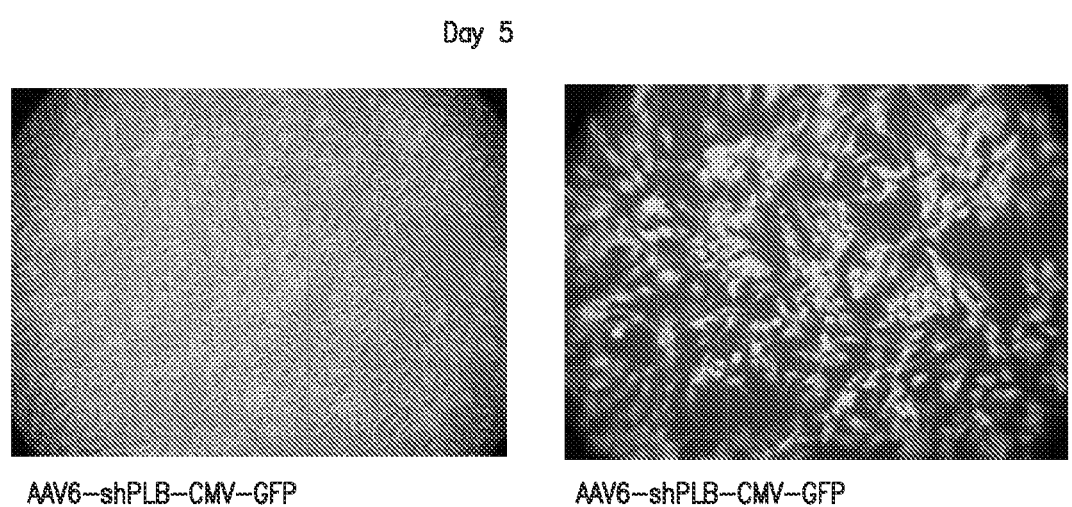

FIG. 5B is a pictorial diagram showing the cultured cardiomyocyte monolayer on day 5 after incubation with the AAV6shPLB-CMV-GFP marker vector, conforming to a very high transduction rate for the AAV6 pseudotype.

Figure 5C:

FIG. 5C is a pictorial diagram suggesting a possible cause for disturbed shRNA production in the U6-shPLB-bGH direction in read-through from MCV through the termination signal into the very short shRNA sequence which then impairs proper formation of the short hairpins which mediate RNAi.

Figure 5D:
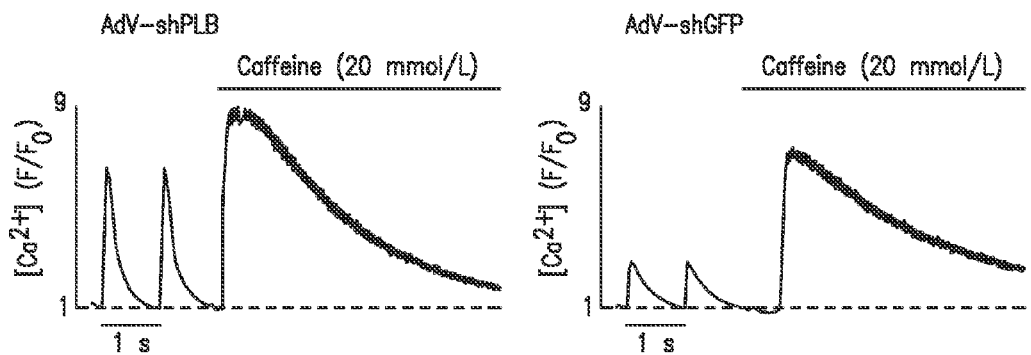

FIG. 5D is a series of graphical diagrams showing alteration of calcium homeostasis in NRCMs during RNAi treatment.

Figure 5E:
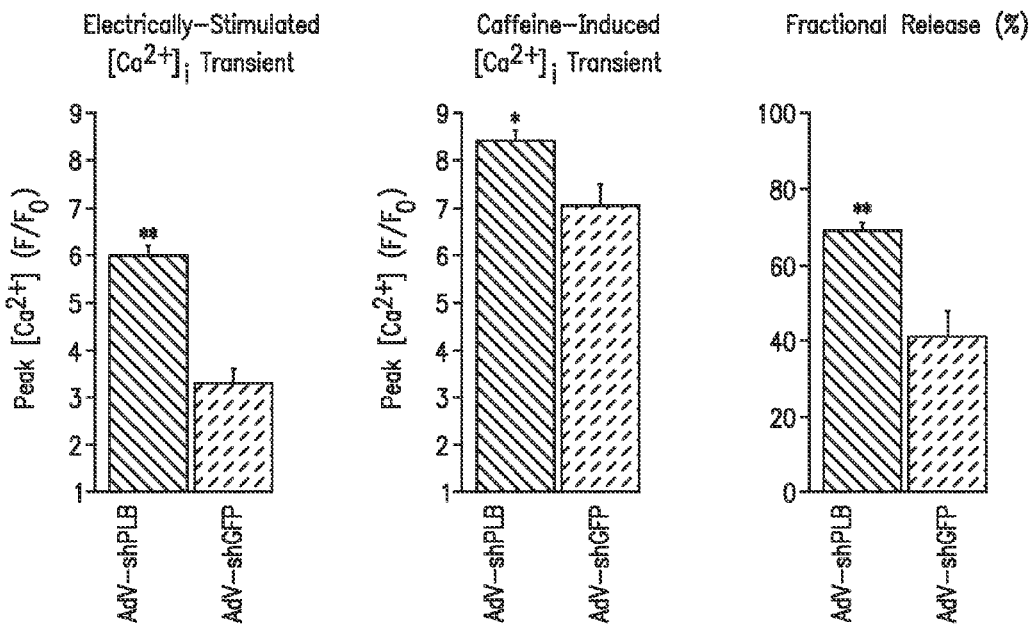

FIG. 5E is a series of graphical diagrams showing alteration of calcium homeostasis in NRCMs during RNAi treatment.

Figure 6:
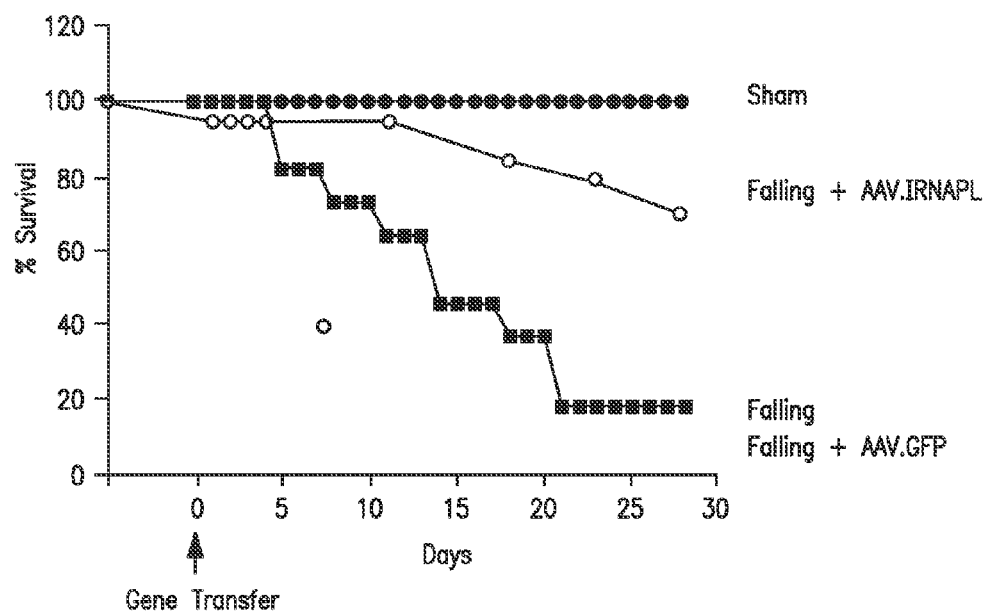

FIG. 6 is a graphical diagram showing improved survival in rats with heart failure and treated with AAV9/PL-RNAi. It shows the effect of inhibition of phospholamban by RNAi gene transfer using expression of AAV9/PL-RNAi on survival in rats with pressure-overload hypertrophy in transition to heart failure, as compared with controls using vector alone or with GFP.

Figure 7:
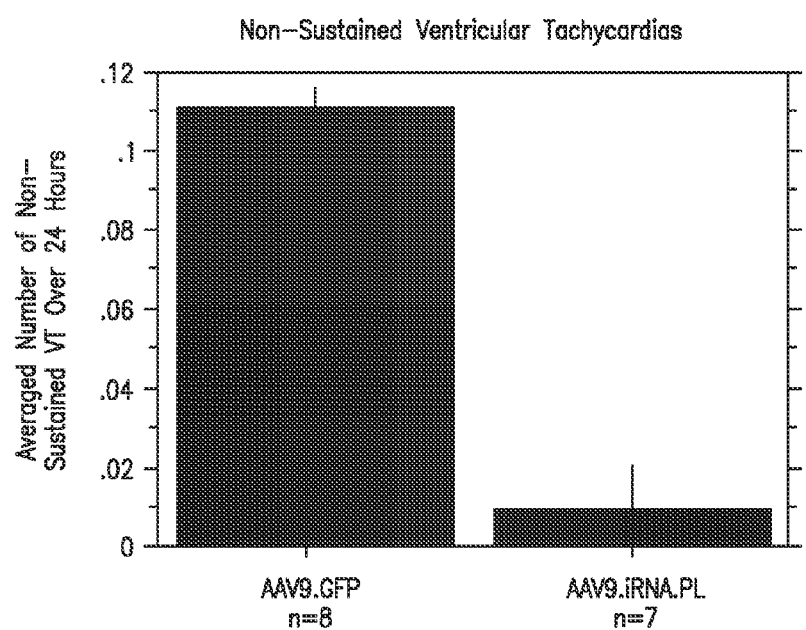

FIG. 7 is a graphical diagram showing results of reduced ventricular arrhythmias in a porcine ischemia reperfusion model. The experiment used expression of AAV9/PL-RNAi as compared with a control vector using GFP.

Figure 8:
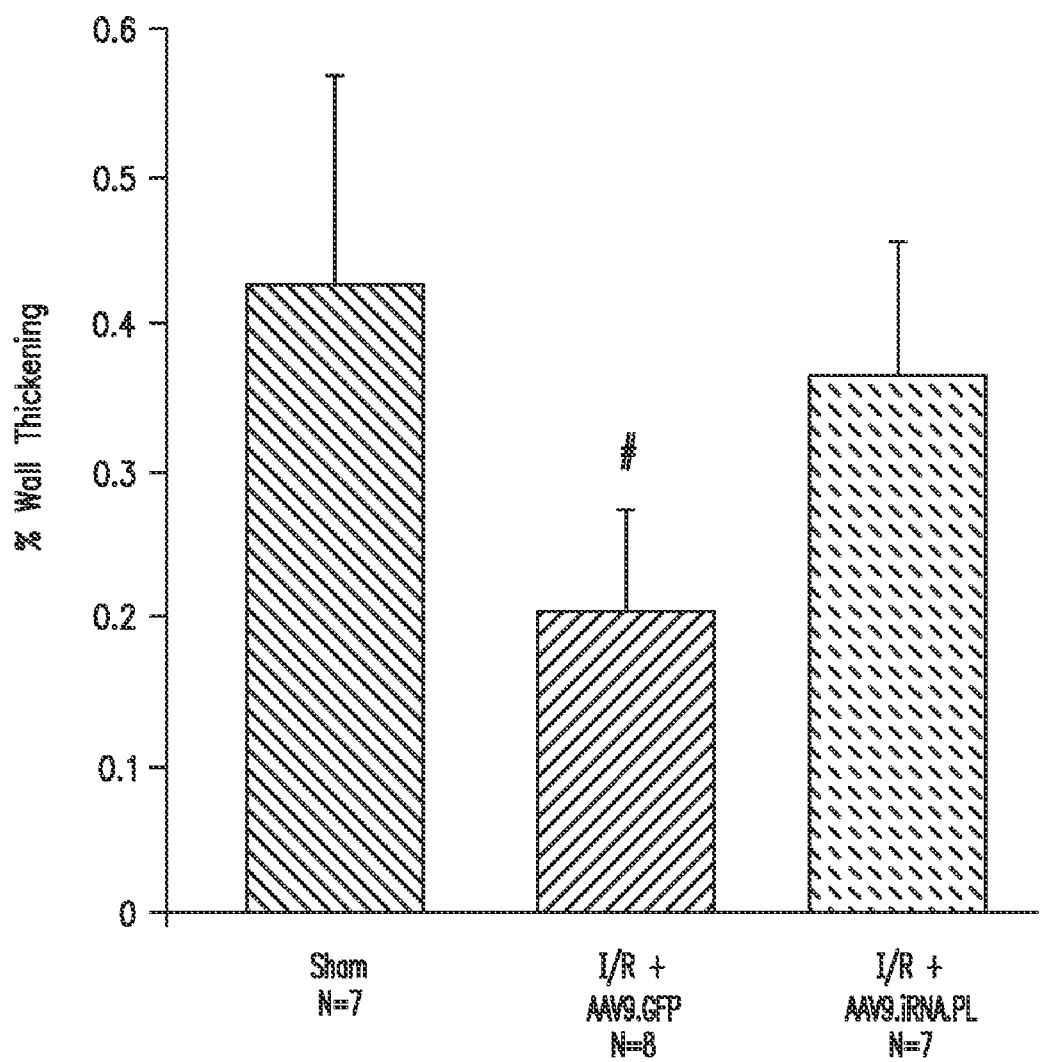

FIG. 8 is a graphical diagram showing results of improved ventricular function in a porcine ischemia reperfusion model. The experiment used expression of AAV9/PL-RNAi as compared with controls using vector alone or with GFP.

DETAILED DESCRIPTION OF THE INVENTION

Before the present composition, methods, and treatment methodology are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, non-limiting methods and materials are now described.

The practice of the present invention will employ, unless otherwise indicated, conventional methods of virology, microbiology, molecular biology and recombinant DNA techniques within the skill of the art. Such techniques are explained fully in the literature; see, e.g., Sambrook, et al. Molecular Cloning: A Laboratory Manual (Current Edition); DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, vol. I & II (P. Tijessen, ed.); Fundamental Virology, 2nd Edition, vol. I & II (B. N. Fields and D. M. Knipe, eds.).

The present invention successfully demonstrates the treatment of heart failure (HF) in a subject using RNAi complementary to PLB, a key regulator of cardiac $Ca^{2+}$ homeostasis. Synthetic small interfering RNAs mediate RNAi, but their use in vivo is limited by instability in plasma and low transfer into target cells. Applicants have demonstrated that an adenoviral short hairpin RNA vector (AdV-shRNA) silenced PLB in cardiomyocytes (PNCMs) and improved hemodynamics in HF animals in vivo. Applicants have also developed a cardiotropic adeno-associated virus (AAV) vector carrying RNAi which achieved restoration of cardiac function, reversal of cardiac dilation and hypertrophy, and improved survival. In PNCMs phenylephrine-induced hypertrophy-related microRNA deregulations were corrected by the RNAi vectors. Beyond their effect on contractile function, RNAi targeting altered microRNA levels thereby changing the cellular transcriptional program directly in the absence of hemodynamic factors or neurohumoral activation.

In one embodiment, a method of treating heart failure is disclosed including, administering to a subject in need thereof a therapeutically effective amount of an RNAi expression cassette, where the cassette includes a virion vector and an RNAi sequence whose expression product decreases expression and/or activity of phospholamban (PLB), in an amount effective to transduce cardiomyocytes of the subject, thereby resulting in expression of the RNAi expression cassette and treating heart failure in the subject.

The present invention discloses a strategy for the treatment of a cardiac disease by locally induced RNAi. HF remains a leading cause of mortality in the developed world. Current drug treatment has limited efficacy and in advanced HF left-ventricular assist devices or heart transplantation are ultimate options. Although HF may result from multiple etiologies, defective cardiac $Ca^{2+}$ homeostasis has been identified as an important final common pathway. Malfunction of the failing heart is in part due to dysfunction of the PLB-controlled sarcoplasmic reticulum $Ca^{2+}$ ATPase pump (SERCA2a) resulting from reduced SERCA2a expression and/or PLB phosphorylation (Schmidt et al., *Am J Physiol* (1999) 277: H474-480). Unphosphorylated PLB keeps the $Ca^{2+}$ affinity of SERCA2a low, resulting in decreased SR $Ca^{2+}$ uptake, slowed relaxation and decreased SR $Ca^{2+}$ load, while PLB phosphorylation in response to β-adrenergic stimulation relieves this inhibition (MacLennan, D. H. & Kranias, E. G. Phospholamban: a crucial regulator of cardiac contractility. *Nature Reviews Molecular Cell Biology* 4, 566-77 (2003)). Germline ablation of the PLB gene (Luo et al., *Circ Res* (1994) 75:401-409), and somatic gene transfer for dominant negative PLB mutants (Hoshijima et al., *Mature Medicine* (2002) 8:864-871; Iwanaga et al., *J Clin Invest* (2004) 113: 727-736), PLB-antisense-RNAs (Eizema et al., *Circulation* (2000) 101:2193-2199; He et al., *Circulation* (1999) 100: 974-980), or intracellular inhibitory PLB antibodies were employed to increase SERCA2a activity, contractile function and to rescue heart failure models (Dieterle et al., *Cardiovasc Res* (2005) 67:678-688; Meyer et al., *FASEB J* (2004) 18:1312-1314; Minamisawa, S. et al. Chronic phospholamban-sarcoplasmic reticulum calcium ATPase interaction is the critical calcium cycling defect in dilated cardiomyopathy. *Cell* 99, 313-22 (1999)). RNAi mediated by chemically synthesized short interfering RNAs (siRNAs) in cardiomyocytes showed low efficacy and stability even in vitro (Watanabe et al, *J Mol Cell Cardiol* (2004) 37:691-698).

Two fundamental limitations of synthetic siRNAs are their rapid degradation in plasma and target cells, and the problem of achieving adequate transfer and targeting in vivo. Viral vectors have the potential to overcome these limitations. In the present invention, no change in the expression of other cardiac proteins including $Ca^{2+}$ handling proteins occurred indicating high target specificity. As such, functional characterization of a series of vectors and the determinants of their efficacy was followed by determination of an optimized parvovirus (i.e., AAV) alongside a traditional adenoviral vector in an animal model of severe HF, and of cardiomyocyte microRNA (miR) pathways during RNAi therapy. As such, the data presented herein demonstrates in vivo restoration of cardiac function and reduction of pathological hypertrophy and dilation.

The term "parvovirus" as used herein encompasses the family Parvoviridae, including autonomously replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B19 virus, and any other autonomous parvovirus. Other autonomous parvoviruses are known to those skilled in the art. See, e.g., BERNARD N. FIELDS et al., *VIROLOGY*, volume 2, chapter 69 (4th ed., Lippincott-Raven Publishers).

The Parvoviridae is a family of small single-stranded, non-enveloped DNA viruses with genomes approximately 5000 nucleotides long. Included among the family members are adenovirus (Ad) and adeno-associated virus (AAV). Adenovirus represents a group of viruses that infect the membranes of the respiratory tract, the eyes, the intestines, and the urinary tract. Adenoviruses represent the largest nonenveloped viruses, because they are the maximum size able to be transported through the endosome (i.e. envelope fusion is not necessary). The virion also has a unique "spike" or fibre associated with each penton base of the capsid that aids in attachment to the host cell. AAV is a dependent parvovirus that by definition requires co-infection with another virus (typically an adenovirus or herpesvirus) to initiate and sustain a productive infectious cycle. In the absence of such a helper virus, AAV is still competent to infect or transduce a target cell by receptor-mediated binding and internalization, penetrating the nucleus in both non-dividing and dividing cells.

Once in the nucleus, the virus uncoats and the transgene is expressed from a number of different forms—the most persistent of which are circular monomers. AAV will integrate into the genome of 1-5% of cells that are stably transduced (Nakai et al., *J. Virol.* 76: 11343-349, 2002). Expression of the transgene can be exceptionally stable and in one study with AAV delivery of Factor IX, a dog model continues to express therapeutic levels of the protein 4.5 years after a single direct infusion with the virus. Because progeny virus is not produced from AAV infection in the absence of helper virus, the extent of transduction is restricted only to the initial cells that are infected with the virus. It is this feature which makes AAV a suitable gene therapy vector for the present invention. Furthermore, unlike retrovirus, adenovirus, and herpes simplex virus, AAV appears to lack human pathogenicity and toxicity (Kay et al., *Nature* 424: 251, 2003 and Thomas et al., *Nature Reviews, Genetics* 4: 346-58, 2003).

Typically, the genome of AAV contains only two genes. The "rep" gene codes for at least four separate proteins utilized in DNA replication. The "cap" gene product is spliced differentially to generate the three proteins that comprise the capsid of the virus. When packaging the genome into nascent virus, only the Inverted Terminal Repeats (ITRs) are obligate sequences; rep and cap can be deleted from the genome and be replaced with heterologous sequences of choice. However, in order to produce the proteins needed to replicate and package the AAV-based heterologous construct into nascent virion, the rep and cap proteins must be provided in trans. The helper functions normally provided by co-infection with the helper virus, such as adenovirus or herpesvirus, also can be provided in trans in the form of one or more DNA expression plasmids. Since the genome normally encodes only two genes it is not surprising that, as a delivery vehicle, AAV is limited by a packaging capacity of 4.5 single stranded kilobases (kb). However, although this size restriction may limit the genes that can be delivered for replacement gene therapies, it does not adversely affect the packaging and expression of shorter sequences such as RNAi.

The utility of AAV for RNAi applications was demonstrated in experiments where AAV was used to deliver shRNA in vitro to inhibit p53 and Caspase 8 expression (Tomar et al., *Oncogene* 22: 5712-15, 2003). Following cloning of the appropriate sequences into a gutted AAV-2 vector, infectious AAV virions were generated in HEK293 cells and used to infect HeLa S3 cells. A dose-dependent decrease of endogenous Caspase 8 and p53 levels was demonstrated. Boden et al. also used AAV to deliver shRNA in vitro to inhibit HIV replication in tissue culture systems (Boden et al., *J. Virol.* 77(21): 115231-35, 2003) as assessed by p24 production in the spent media.

However, technical hurdles must be addressed when using AAV as a vehicle for RNAi expression constructs. For example, various percentages of the human population may possess neutralizing antibodies against certain AAV serotypes. However, since there are several AAV serotypes, some of which the percentage of individuals harboring neutralizing antibodies is vastly reduced, other serotypes can be used or pseudo-typing may be employed. There are at least nine different serotypes that have been characterized, with dozens of others which have been isolated but have been less well described. Another limitation is that as a result of a possible immune response to AAV, AAV-based therapy may only be administered once; however, use of alternate, non-human derived serotypes may allow for repeat administrations. Administration route, serotype, and composition of the delivered genome all influence tissue specificity.

Another limitation in using unmodified AAV systems with the RNAi expression constructs is that transduction can be inefficient. Stable transduction in vivo may be limited to 5-10% of cells. However, different methods are known in the art to boost stable transduction levels. One approach is utilizing pseudotyping, where AAV-2 genomes are packaged using cap proteins derived from other serotypes. For example, by substituting the AAV-5 cap gene for its AAV-2 counterpart, Mingozzi et al. increased stable transduction to approximately 15% of hepatocytes (Mingozzi et al., *J. Virol.* 76(20): 10497-502, 2002). Thomas et al., transduced over 30% of mouse hepatocytes in vivo using the AAV8 capsid gene (Thomas et al., *J. Virol.* in press). Grimm et al. (*Blood.* 2003-02-0495) exhaustively pseudotyped AAV-2 with AAV-1, AAV-3B, AAV-4, AAV-5, and AAV-6 for tissue culture studies. The highest levels of transgene expression were induced by virion which had been pseudotyped with AAV-6; producing nearly 2000% higher transgene expression than AAV-2. Thus, the present invention contemplates use of a pseudotyped AAV virus to achieve high transduction levels, with a corresponding increase in the expression of the RNAi multiple-promoter expression constructs.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, ovine AAV, and any other AAV now known. See, e.g., BERNARD N. FIELDS et al., *VIROLOGY*, volume 2, chapter 69 (4th ed., Lippincott-Raven Publishers). Recently, a number of putative new AAV serotypes and clades have been identified (see, e.g., Gao et al., (2004) *J. Virology* 78:6381-6388; Moris et al., (2004) *Virology* 33-:375-383). In one embodiment, the AAV is AAV type 9.

The genomic sequences of the various serotypes of AAV and the autonomous parvoviruses, as well as the sequences of the terminal repeats (TRs), Rep proteins, and capsid subunits are known in the art. Such sequences may be found in the literature or in public databases such as GenBank, including but not limited to, GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC_001358, NC_001540, AF513851, AF513852, AY530579; the disclosures of which are incorporated by reference herein for teaching parvovirus and AAV nucleic acid and amino acid sequences. See also, e.g., Srivistava et al., (1983) *J. Virology* 45:555; Chiorini et al., (1998) *J. Virology* 71:6823; Chiorini et al., (1999) *J. Virology* 73:1309; Bantel-Schaal et al., (1999) *J. Virology* 73:939; Xiao et al., (1999) *J. Virology* 73:3994; Muramatsu et al., (1996) *Virology* 221:208; Shade et al., (1986) *J. Virol.* 58:921; Gao et al., (2002) *Proc. Nat. Acad. Sci. USA* 99:11854; Moris et al., (2004) *Virology* 33-:375-383; international patent publications WO 00/28061, WO 99/61601, WO 98/11244; and U.S. Pat. No. 6,156,303, incorporated herein by reference.

The term "tropism" as used herein refers to preferential entry of the virus into certain cells or tissues, optionally followed by expression (e.g., transcription and, optionally, translation) of a sequence(s) carried by the viral genome in the cell, e.g., for a recombinant virus, expression of the heterologous nucleotide sequence(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus, from a non-integrated episome, as well as any other form in which the virus may take within the cell.

As used herein, the term "polypeptide" encompasses both peptides and proteins (including naturally occurring or non-naturally occurring), unless indicated otherwise.

As used herein, an "isolated" polypeptide (e.g., an "isolated peptide" or an "isolated protein") means a polypeptide at least partially separated from at least some of the other components of the naturally occurring organism or virus, for example, the cell or viral structural components or other polypeptides or nucleic acids commonly found associated with the polypeptide.

A "polynucleotide" is a sequence of nucleotide bases, and may be RNA, DNA or DNA-RNA hybrid sequences (including both naturally occurring and non-naturally occurring nucleotide), but in representative embodiments are either single or double stranded DNA sequences.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide.

As used herein, by "isolate" or "purify" (or grammatical equivalents) a virus vector, it is meant that the virus vector is at least partially separated from at least some of the other components in the starting material.

A "therapeutic polypeptide" is a polypeptide that can alleviate or reduce symptoms that result from an absence or defect in a protein in a cell or subject. Alternatively, a "therapeutic polypeptide" is one that otherwise confers a benefit to a subject, e.g., anti-arrythmia effects or improvement in survivability from heart failure.

"Transfection" is used to refer to the uptake of nucleic acid compositions by a cell. A cell has been "transfected" when an exogenous nucleic acid composition has crossed the cell membrane. A number of transfection techniques are generally known in the art. See, e.g., [69, 70], Sambrook et al. (1989) Molecular Cloning, a laboratory manual, Cold Spring Harbor Laboratories, New York, Davis et al. (1986) Basic Methods in Molecular Biology, Elsevier, and [71]. Such techniques can be used to introduce one or more nucleic acid compositions, such as a plasmid vector and other nucleic acid molecules, into suitable host cells. The term refers to both stable and transient uptake of the genetic material. For purposes of this invention, "transduction" is a special form of "transfection" via a viral vector.

"Transduction" denotes the delivery of a nucleic acid composition to, into or within a recipient cell either in vivo, in vitro or ex vivo, via a virus or viral vector, such as via a recombinant AAV virion. Transduction is a special form of transfection, i.e., the term transfection includes the term transduction.

By the term "treating" including grammatical equivalents thereof, it is meant that the severity of the subject's condition is reduced or at least partially improved or ameliorated and/or that some alleviation, mitigation or decrease in at least one clinical symptom is achieved and/or there is a delay in the progression of the condition and/or prevention or delay of the onset of a disease or disorder. Thus, the term "treating" refers to both prophylactic and therapeutic regimens.

A "heterologous nucleotide sequence" or "heterologous nucleic acid" is a sequence that is not naturally occurring in the virus. Generally, the heterologous nucleic acid comprises an open reading frame that encodes a polypeptide or non-translated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within an AAV capsid. Alternatively, in some contexts, the term "vector" may be used to refer to the vector genome/vDNA alone.

A "rAAV vector genome" or "rAAV genome" is an AAV genome (i.e., vDNA) that comprises one or more heterologous nucleotide sequences. rAAV vectors generally require only the 145 base terminal repeat(s) (TR(s)) in cis to generate virus. All other viral sequences are dispensable and may be supplied in trans (Muzyczka, (1992) Curr. Topics Microbiol. Immunol. 158:97). Typically, the rAAV vector genome will only retain the minimal TR sequence(s) so as to maximize the size of the transgene that can be efficiently packaged by the vector. The structural and non-structural protein coding sequences may be provided in trans (e.g., from a vector, such as a plasmid, or by stably integrating the sequences into a packaging cell). The rAAV vector genome comprises at least one TR sequence (e.g., AAV TR sequence), optionally two TRs (e.g., two AAV TRs), which typically will be at the 5' and 3' ends of the heterologous nucleotide sequence(s), but need not be contiguous thereto. The TRs can be the same or different from each other.

An "AAV terminal repeat" or "AAV TR" may be from any AAV, including but not limited to serotypes 1, 2, 3, 4, 5, 6, 7, 8, 9, 10 or 11. The AAV terminal repeats need not have a wild-type terminal repeat sequence (e.g., a wild-type sequence may be altered by insertion, deletion, truncation or missense mutations), as long as the terminal repeat mediates the desired functions, e.g., replication, virus packaging, integration, and/or provirus rescue, and the like.

The term "terminal repeat" or "TR" includes any viral terminal repeat and synthetic sequences that form hairpin structures and function as an inverted terminal repeat, such as the "double-D sequence" as described in U.S. Pat. No. 5,478, 745 to Samulski et al. The capsid structures of autonomous parvoviruses and AAV are described in more detail in BERNARD N. FIELDS et al., *VIROLOGY*, volume 2, chapters 69 & 70 (4th ed., Lippincott-Raven Publishers). See also, description of the crystal structure of AAV2 (Xie et al., (2002) Proc. Nat. Acad. Sci. 99:10405-10), AAV4 (Padron et al., (2005) *J. Virol.* 79: 5047-58), AAV5 (Walters et al., (2004) *J. Virol.* 78: 3361-71) and CPV (Xie et al., (1996) *J. Mol. Biol.* 6:497-520 and Tsao et al., (1991) *Science* 251: 1456-64). An "AAV minigene" refers to a construct composed of, at a minimum, AAV ITRs and a heterologous nucleic acid composition. For production of rAAV according to the invention, a minigene may be carried on any suitable vector, including viral vectors, plasmid vectors, and the like.

The virus vectors of the invention can further be "targeted" virus vectors (e.g., having a directed tropism) and/or a "hybrid" parvovirus (i.e., in which the rAAV genome and viral capsid are from different parvoviruses) as described in international patent publication WO 00/28004 and Chao et al., (2000) *Molecular Therapy* 2:619.

The virus vectors of the invention can further be duplexed parvovirus particles as described in International Patent Application Publication No. WO 01/92551. Thus, in some embodiments, double stranded (duplex) genomes can be packaged into the virus capsids of this invention.

Further, the viral capsid or genome can contain other modifications, including insertions, deletions and/or substitutions.

Accordingly, as used herein, the term "virus vector" encompasses hybrid, targeted and duplexed virus particles, as well as other modified forms of parvoviruses and AAV.

As used herein, the term "vertebrate animal" encompasses mammals, avian species, fish or reptiles. For example, the vertebrate animal may be a mammal. The term "Mammals" includes humans and non-human primates, livestock animals (e.g. sheep, cow, goat, pig, donkey, horse), laboratory test animals (e.g. rat, mouse, rabbit, guinea pig, hamster), companion animals (e.g. dog, cat) or captured wild animals. Mammals include, but are not limited to, human and murine mammals.

The present invention is predicated, in part, on the application of agents which facilitate gene silencing via RNAi to downregulate or silence one or more transcriptionally active genetic regions which are directly or indirectly associated with the modulation of calcium flux in cardiac cells as a method to treat heart failure. In one embodiment, a method of treating heart failure is disclosed including, administering to a subject in need thereof a therapeutically effective amount of an RNAi expression cassette, where the cassette includes a virion vector and an RNAi sequence whose expression product decreases expression of phospholamban (PLB) mRNA, in an amount effective to transduce cardiomyocytes of the subject, thereby resulting in expression of the RNAi expression cassette and treating heart failure in the subject.

The term "RNA interference" refers generally to a process in which a double-stranded RNA molecule changes the expression of a nucleic acid sequence with which the double-stranded or short hairpin RNA molecule shares substantial or total homology. While not being bound by theory, the mechanism of action may include, but is not limited to, direct or indirect down regulation of the expression of the PLB gene, decrease in PLB mRNA, and/or a decrease in PLB activity. The term "RNAi" refers to an RNA sequence that elicits RNA interference, and which is transcribed from a vector. The terms "short hairpin RNA" or "shRNA" refer to an RNA structure having a duplex region and a loop region. This term should also be understood to specifically include RNA molecules with stem-loop or panhandle secondary structures. In some embodiments of the present invention, RNAis are expressed initially as shRNAs.

The term "RNAi expression cassette" refers to a cassette according to embodiments of the present invention having at least one [promoter-RNAi-terminator] unit. The term "multiple promoter RNAi expression cassette" refers to an RNAi expression cassette comprising two or more [promoter-RNAi-terminator] units. The terms "RNAi expression construct" or "RNAi expression vector" refer to vectors containing at least one RNAi expression cassette.

RNAi is generally optimised by identical sequences between the target and the RNAi. The RNA interference phenomenon can be observed with less than 100% homology, but the complementary regions must be sufficiently homologous to each other to form the specific double stranded regions. The precise structural rules to achieve a double-stranded region effective to result in RNA interference have not been fully identified, but approximately 70% identity is generally sufficient. Accordingly, in some embodiments of the invention, the homology between the RNAi and PLB is at least 70% nucleotide sequence identity, and may be at least 75% nucleotide sequence identity. Homology includes, but is not limited to, at least 80% nucleotide sequence identity, and is at least 85% or even 90% nucleotide sequence identity. In one embodiment, sequence homology between the target sequence and the sense strand of the RNAi is at least 90%, 91%, 92%, 93%, 94%, 95%, 96%, 97%, 98%, 99% or 100% nucleotide sequence identity.

Another consideration is that base-pairing in RNA is subtly different from DNA in that G will pair with U, although not as strongly as it does with C, in RNA duplexes. Moreover, for RNAi efficacy, it is more important that the antisense strand be homologous to the target sequence. In some circumstances, it is known that 17 out of 21 nucleotides is sufficient to initiate RNAi, but in other circumstances, identity of 19 or 20 nucleotides out of 21 is required. While not being bound by theory, at a general level, greater homology is required in the central part of a double stranded region than at its ends. Some predetermined degree of lack of perfect homology may be designed into a particular construct so as to reduce its RNAi activity which would result in a partial silencing or repression of the target gene's product, in circumstances in which only a degree of silencing was sought. In such a case, only one or two bases of the antisense sequence may be changed. On the other hand, the sense strand is more tolerant of mutations. While not being bound by theory, this may be due to the antisense strand being the one that is catalytically active. Thus, less identity between the sense strand and the transcript of a region of a target gene will not necessarily reduce RNAi activity, particularly where the antisense strand perfectly hybridizes with that transcript. Mutations in the sense strand (such that it is not identical to the transcript of the region of the target gene) may be useful to assist sequencing of hairpin constructs and potentially for other purposes, such as modulating dicer processing of a hairpin transcript or other aspects of the RNAi pathway.

The terms "hybridizing" and "annealing" including grammatical equivalents thereof, are used interchangeably in this specification with respect to nucleotide sequences and refer to nucleotide sequences that are capable of forming Watson-Crick base pairs due to their complementarity. The person skilled in the art would understand that non-Watson-Crick base-pairing is also possible, especially in the context of RNA sequences. For example a so-called "wobble pair" can form between guanosine and uracil residues in RNA.

The RNA expression products of the RNAi expression cassette lead to the generation of a double-stranded RNA (dsRNA) complex for inducing RNA interference and thus down-regulating or decreasing expression of a mammalian gene. "dsRNA" refers to a ribonucleic acid complex comprising two Watson-Crick base-paired complementary RNA strands. The dsRNA complex comprises a first nucleotide sequence that hybridizes under stringent conditions, including a wash step of $0.2 \times SSC$ at $65°C$., to a nucleotide sequence of at least one mammalian gene and a second nucleotide sequence which is complementary to the first nucleotide sequence. The first nucleotide sequence might be linked to the second nucleotide sequence by a third nucleotide sequence (e.g., an RNA loop) so that the first nucleotide sequence and the second nucleotide sequence are part of the same RNA molecule; alternatively, the first nucleotide sequence might be part of one RNA molecule and the second nucleotide sequence might be part of another RNA molecule. Thus, a dsRNA complex may be formed by intramolecular hybridization or annealing or the ds RNA complex is formed by intermolecular hybridization or annealing.

"Complementary" is used herein in its usual way to indicate Watson-Crick base pairing, and "non-complementary" is used to mean non-Watson-Crick base pairing, even though such non-complementary sequences may form wobble pairs or other interactions. However, in the context of the present invention, reference to "non-pairing" sequences relates specifically to sequences between which Watson-Crick base pairs do not form. Accordingly, embodiments of spacing or bubble sequences according to the present invention are described and illustrated herein as non-pairing sequences, regardless of whether non-Watson-Crick base pairing could theoretically or does in practice occur.

Terms used to describe sequence relationships between two or more polynucleotides include "reference sequence," "comparison window," "sequence similarity," "sequence identity," "percentage of sequence similarity," "percentage of sequence identity," "substantially similar," and "substantial identity." A "reference sequence" is at least 10 but frequently 15 to 25 and often greater than 25 or above, such as 30 monomer units, inclusive of nucleotides, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically at least about 10 contiguous residues that is compared to a reference sequence. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerised implementations of algorithms (e.g., GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al. A detailed discussion of sequence analysis can be found in Unit 19.3 of Ausubel et al. For example, "percentage of sequence identity," may be calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software.

Alternatively, homology/identity for polynucleotides can be determined by hybridization experiments. As used herein, a first nucleic acid sequence or fragment (such as for example, primers or probes), is considered to selectively hybridize to a second nucleic acid sequence, thus indicating "substantial homology," if such a second sequence is capable of specifically hybridizing to the first sequence or a variant or capable of specifically priming a polymerase chain reaction: (i) under typical hybridization and wash conditions, such as those described, for example, in Maniatis, (Molecular Cloning: A Laboratory Manual, $2^{nd}$ Edition, 1989) where hybridization conditions may be those of lesser stringency or, higher stringency; or (ii) using stringent wash conditions that allow at most about 25-30% basepair mismatches, for example, 2×SSC, 0.1% SDS, at room temperature twice, for 30 minutes each; then 2×SSC, 0.1% SDS, 37° C., once for 30 minutes; the 2×SSC at room temperature twice, 10 minutes each or (iii) under standard PCR conditions or under "touch-down" PCR conditions.

The term "hybridizing conditions" as used herein shall mean conditions permitting hybridization between two complementary strands of nucleic acid in general, and between two complementary strands of RNA having a length of at least seven nucleotides in particular. Hybridizing conditions are well known in the art, and include, without limitation, physiological conditions, such as, but not limited to, intracellular physiological conditions.

The RNAi of the present invention may comprise short, double-stranded, or partially double-stranded (e.g., panhandle, stem-loop and hairpin) RNAs that are not toxic in normal mammalian cells. There is no particular limitation in the length of the RNAi of the present invention as long as they do not show cellular toxicity. RNAi may be, for example, about 10 to 71 bp in length, about 15 to 49 bp in length, about 15 to 35 bp in length, and about 19 to 29 bp in length or about 19 to 21 bp in length. The double-stranded RNA portions of RNAi may be completely homologous, or may contain non-paired portions due to sequence mismatch (the corresponding nucleotides on each strand are not complementary), bulge (lack of a corresponding complementary nucleotide on one strand), and the like. Such non-paired portions can be tolerated to the extent that they do not significantly interfere with RNAi duplex formation or efficacy.

"siRNAs" or short interfering RNAs may be manufactured by methods known in the art such as by typical oligonucleotide synthesis, and often will incorporate chemical modifications to increase half life and/or efficacy of the siRNA, and/or to allow for a more robust delivery formulation. Many modifications of oligonucleotides are known in the art. For example, U.S. Pat. No. 6,620,805 discloses an oligonucleotide that is combined with a macrocycle having a net positive charge such as a porphyrin; U.S. Pat. No. 6,673,611 discloses various formulas; US Patent Application Publication Nos. 2004/0171570, 2004/0171032, and 2004/0171031 disclose oligomers that include a modification comprising a polycyclic sugar surrogate; such as a cyclobutyl nucleoside, cyclopentyl nucleoside, proline nucleoside, cyclohexene nucleoside, hexose nucleoside or a cyclohexane nucleoside; and oligomers that include a non-phosphorous-containing internucleoside linkage; US Patent Application Publication No. 2004/0171579 discloses a modified oligonucleotide where the modification is a 2' constituent group on a sugar moiety that is not H or OH; US Patent Application Publication No. 2004/0171030 discloses a modified base for binding to a cytosine, uracil, or thymine base in the opposite strand comprising a boronated C and U or T modified binding base having a boron-containing substituent selected from the group consisting of —$BH_2CN$, —$BH_3$, and —$BH_2COOR$, wherein R is C1 to C18 alkyl; US Patent Application Publication No. 2004/0161844 discloses oligonucleotides having phosphoramidate internucleoside linkages such as a 3'amino-phosphoramidate, aminoalkylphosphoramidate, or aminoalkylphosphorthioamidate internucleoside linkage; US Patent Application Publication No. 2004/0161844 discloses yet other modified sugar and/or backbone modifications, where in some embodiments, the modification is a peptide nucleic acid, a peptide nucleic acid mimic, a morpholino nucleic acid, hexose sugar with an amide linkage, cyclohexenyl nucleic acid (CeNA), or an acyclic backbone moiety; US Patent Application Publication No. 2004/0161777 discloses oligonucleotides with a 3' terminal cap group; US Patent Application Publication No. 2004/0147470 discloses oligomeric compounds that include one or more cross-linkages that improve nuclease resistance or modify or enhance the pharmacokinetic and phamacodynamic properties of the oligomeric compound where such cross-linkages comprise a disulfide, amide, amine, oxime, oxyamine, oxyimine, morpholino, thioether, urea, thiourea, or sulfonamide moiety; US Patent Application Publication No. 2004/0147023 discloses a gapmer comprising two terminal RNA segments having nucleotides of a first type and an internal RNA segment having nucleotides of a second type where nucleotides of said first type independently include at least one sugar substituent where the sugar substituent comprises a halogen, amino, trifluoroalkyl, trifluoroalkoxy, azido, aminooxy, alkyl, alkenyl, alkynyl, O-, S-, or N(R*)-alkyl; O-, S-, or N(R*)-alkenyl; O-, S- or N(R*)-alkynyl; O-, S- or N-aryl, O-, S-, or N(R*)-aralkyl group; where the alkyl, alkenyl, alkynyl, aryl or aralkyl may be a substituted or unsubstituted alkyl, alkenyl, alkynyl, aralkyl; and where, if substituted, the substitution is an alkoxy, thioalkoxy, phthalimido, halogen, amino, keto, carboxyl, nitro, nitroso, cyano, trifluoromethyl, trifluoromethoxy, imidazole, azido, hydrazine, aminooxy, isocyanato, sulfoxide, sulfone, disulfide, silyl, heterocycle, or carbocycle group, or an intercalator, reporter group, conjugate, polyamine, polyamide, polyalkylene glycol, or a polyether of the formula (—O-alkyl)$_m$, where m is 1 to about 10; and R* is hydrogen, or a protecting group; or US Patent Application Publication No. 2004/0147022 disclosing an oligonucleotide with a modified sugar and/or backbone modification, such as a 2'-$OCH_3$ substituent group on a sugar moiety.

Accordingly, in one aspect, the present invention discloses a method for treating heart failure including, administering to a subject in need thereof a therapeutically effective amount of an RNAi expression cassette, where the cassette includes a virion vector and an RNAi sequence whose expression product decreases expression of phospholamban (PLB) mRNA, in an amount effective to transduce cardiomyocytes of the subject, thereby resulting in expression of the RNAi expression cassette and treating heart failure in the subject.

Reference herein to a "promoter" or "promoter sequence" is to be taken in its broadest context and includes a DNA regulatory region capable of binding RNA polymerase in a cell and initiating transcription of a polynucleotide or polypeptide coding sequence such as messenger RNA, ribosomal RNAs, small nuclear of nucleolar RNAs or any kind of RNA transcribed by any class of any RNA polymerase. "Promoters" contemplated herein may also include the transcriptional regulatory sequences of a classical genomic gene, including the TATA box which is required for accurate transcription initiation in eukaryotic cells, with or without a CCAAT box sequence and additional regulatory elements (i.e., upstream activating sequences, enhancers and silencers).

A promoter is usually, but not necessarily, positioned upstream or 5', of the sequence which it regulates. Furthermore, the regulatory elements comprising a promoter are usually positioned within 2 kb of the start site of transcription of the sequence to be regulated.

In the present context, the term "promoter" is also used to describe a synthetic or fusion molecule or derivative which confers, activates or enhances expression of an isolated nucleic acid molecule in a mammalian cell. Another or the same promoter may also be required to function in plant, animal, insect, fungal, yeast or bacterial cells. Promoters may contain additional copies of one or more specific regulatory elements to further enhance expression of a structural gene, which in turn regulates and/or alters the spatial expression and/or temporal expression of the gene. For example, regulatory elements which confer inducibility on the expression of the structural gene may be placed adjacent to a heterologous promoter sequence driving expression of a nucleic acid molecule.

Placing a sequence under the regulatory control of a promoter sequence means positioning said molecule such that expression is controlled by the promoter sequence. Promoters are generally positioned 5' (upstream) to the genes that they control. In the construction of heterologous promoter/structural gene combinations, generally promoter position may be a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the positioning of a regulatory sequence element with respect to a heterologous gene to be placed under its control is defined by the positioning of the element in its natural setting, i.e., the genes from which it is derived. Again, as is known in the art, some variation in this distance can also occur.

The promoter may regulate the expression of a sequence constitutively, or differentially with respect to the cell, tissue or organ in which expression occurs, or with respect to the developmental stage at which expression occurs, or in response to stimuli such as physiological stresses, regulatory proteins, hormones, pathogens or metal ions, amongst others.

Promoters useful in some embodiments of the present invention may be tissue-specific or cell-specific. The term "tissue specific" as it applies to a promoter refers to a promoter that is capable of directing selective expression of a nucleotide sequence of interest to a specific type of tissue (e.g., muscle tissue), in the relative absence of expression of the same nucleotide sequence of interest in a different type of tissue (e.g., heart). The term "cell-specific" as applied to a promoter refers to a promoter which is capable of directing selective expression of a nucleotide sequence of interest in a specific type of cell in the relative absence of expression of the same nucleotide sequence of interest in a different type of cell within the same tissue (see, e.g., Higashibata et al., *J. Bone Miner. Res.* 19(1): 78-88, 2004; Hoggatt et al., *Circ. Res.* 91(12): 1151-59, 2002; Sohal et al., *Circ. Res.* 89(1): 20-25, 2001; and Zhang et al., *Genome Res.* 14(1): 79-89, 2004). The term "cell-specific" when applied to a promoter also means a promoter capable of promoting selective expression of a nucleotide sequence of interest in a region within a single tissue. Alternatively, promoters may be constitutive or regulatable. Additionally, promoters may be modified so as to possess different specificities.

The term "constitutive" when made in reference to a promoter means that the promoter is capable of directing transcription of an operably linked nucleic acid sequence in the absence of a specific stimulus (e.g., heat shock, chemicals, light, and the like). Typically, constitutive promoters are capable of directing expression of a coding sequence in substantially any cell and any tissue. The promoters used to transcribe RNAi may be constitutive promoters, such as the promoters for ubiquitin, CMV, β-actin, histone H4, EF-1α or pgk genes controlled by RNA polymerase II, or promoter elements controlled by RNA polymerase I. In other embodiments, a Pol II promoter such as CMV, SV40, U1, β-actin or a hybrid Pol II promoter is employed. In other embodiments, promoter elements controlled by RNA polymerase III are used, such as the U6 promoters (e.g., U6-1, U6-8, U6-9), H1 promoter, 7SL promoter, the human Y promoters (hY1, hY3, hY4 (see Maraia et al., *Nucleic Acids Res* 22(15): 3045-52, 1994) and hY5 (see Maraia et al., *Nucleic Acids Res* 24(18): 3552-59, 1994), the human MRP-7-2 promoter, Adenovirus VA1 promoter, human tRNA promoters, the 5s ribosomal RNA promoters, as well as functional hybrids and combinations of any of these promoters.

Alternatively, in some embodiments it may be optimal to select promoters that allow for inducible expression of the RNAi. A number of systems for inducible expression using such promoters are known in the art, including but not limited to the tetracycline responsive system and the lac operator-repressor system (see WO 03/022052 A1; and US 2002/0162126 A1), the ecdyson regulated system, or promoters regulated by glucocorticoids, progestins, estrogen, RU-486, steroids, thyroid hormones, cyclic AMP, cytokines, the calciferol family of regulators, or the metallothionein promoter (regulated by inorganic metals).

One or more enhancers also may be present in the viral multiple-promoter RNAi expression construct to increase expression of the gene of interest. Enhancers appropriate for use in embodiments of the present invention include the Apo E HCR enhancer, the CMV enhancer that has been described recently (see, Xia et al., *Nucleic Acids Res* 31-17, 2003), and other enhancers known to those skilled in the art.

In the present invention, the promoter may be capable of regulating expression of a nucleic acid molecule in a mammalian cell, at least during the period of time over which the target gene is expressed therein and also immediately preceding the commencement of detectable expression of the target gene in said cell. Promoters may be constitutive, inducible or developmentally regulated.

In the present context, the terms "in operable connection with" or "operably under the control" or similar such as "operably linked to" shall be taken to indicate that expression of the structural gene is under the control of the promoter sequence with which it is spatially connected in a cell.

In some embodiments, promoters of variable strength may be employed within an RNAi expression cassette or between different cassettes in an RNAi expression vector which comprises multiple RNAi expression cassettes. For example, use of two or more strong promoters (such as a Pol III-type promoter) may tax the cell, by, e.g., depleting the pool of available nucleotides or other cellular components needed for transcription. In addition or alternatively, use of several strong promoters may cause a toxic level of expression of RNAi in the cell. Thus, in some embodiments one or more of the promoters in the multiple-promoter RNAi expression cassette may be weaker than other promoters in the cassette, or all promoters in the cassette may express RNAi at less than a maximum rate. Promoters also may or may not be modified using molecular techniques, or otherwise, e.g., through regulation elements, to attain weaker levels of transcription.

The vector also may contain additional genetic elements. The types of elements that may be included in the vector are not limited in any way and may be chosen by one of skill in the art. For example, additional genetic elements may include a reporter gene, such as one or more genes for a fluorescent marker protein such as GFP or RFP; an easily assayed enzyme such as β-galactosidase, luciferase, β-glucuronidase, chloramphenical acetyl transferase or secreted embryonic alkaline phosphatase; or proteins for which immunoassays are readily available such as hormones or cytokines. Other genetic elements that may find use in embodiments of the present invention include those coding for proteins which confer a selective growth advantage on cells such as adenosine deaminase, aminoglycodic phosphotransferase, dihydrofolate reductase, hygromycin-B-phosphotransferase, drug resistance, or those genes coding for proteins that provide a biosynthetic capability missing from an auxotroph. If a reporter gene is included along with the RNAi expression cassette, an internal ribosomal entry site (IRES) sequence can be included. The additional genetic elements may be operably linked with and controlled by an independent promoter/enhancer. In addition, a suitable origin of replication for propagation of the vector in bacteria may be employed. The sequence of the origin of replication generally is separated from the RNAi and other genetic sequences that are to be expressed in the target cell, tissue and/or organ. Such origins of replication are known in the art and include the pUC, Co1E1,2-micron or SV40 origins of replication.

The vectors described herein or parts thereof may also be adapted for integration into the genome of a cell in which it is expressed. Those skilled in the art will be aware that, in order to achieve integration of a genetic sequence or expression cassette into the genome of a host cell, certain additional genetic sequences may be required.

In one embodiment, the effect of the vector is to reduce functional expression of the PLB while not substantially reducing the level of transcription of the PLB. Alternatively or in addition to, the genetic construct including synthetic gene does not result in a substantial reduction in steady state levels of total RNA.

Accordingly, in another aspect, the present invention contemplates an RNAi expression vector wherein the RNAi expression vector comprises one or more RNAi expression cassettes as defined herein.

The RNAi of the present invention, result in or otherwise facilitate an altered capacity for translation of a target transcript for translation into an expression product. Although the expression product is generally a protein, the present invention further contemplates expression products in the form of transcribed non-coding RNAs, eRNAs or introns spliced out of a transcript which are involved in genetic regulation.

Reference to "altered capacity" includes, but is not limited to, a reduction in the level of translation such as from about 10% to about 100% and from about 20% to about 90% relative to a cell which is not genetically modified. In one embodiment, the gene corresponding to the target endogenous sequence is substantially not translated into a proteinaceous product. Conveniently, an altered capacity of translation is determined by any change of phenotype wherein the phenotype, in a non-genetically modified cell, is facilitated by the expression of a gene encoding PLB. Any cell carrying a genetic agent of the present invention is said to be "genetically modified." The genetic modification may be permanent or transient. A transient genetic modification occurs, for example, when a cell takes up a genetic agent and permits the generation of transcript. Alternatively, the genetic agent directly reduces the level of translation such as by the administration of an antisense oligonucleotide or larger nucleic acid molecule. In either case, the molecule facilitates gene silencing mechanisms which, as the cells divide, may be removed. Permanent gene silencing is more likely to occur when the genetic agent integrates into a cell's genome and the agent is passed onto daughter cells.

Standard methods may be used to administer RNAi or RNAi expression constructs to a cell, tissue or organ for the purposes of modulating the expression of the target gene. Useful methods of administration include liposome-mediated transfection or transformation, transformation of cells with attenuated virus particles or bacterial cells, cell mating, transformation or transfection procedures known to those skilled in the art or described by Ausubel et al. (1992). For example, a nucleic acid molecule may be introduced as naked DNA or RNA, optionally encapsulated in a liposome, in a virus particle as attenuated virus or associated with a virus coat or a transport protein or inert carrier such as gold or as a recombinant viral vector or bacterial vector or as a genetic construct, amongst others.

In one embodiment, a viral delivery system based on any appropriate virus may be used to deliver the RNAi expression constructs of the present invention. In addition, hybrid viral systems may be of use. The choice of viral delivery system will depend on various parameters, such as efficiency of delivery into cardiomyocytes or other target tissues, transduction efficiency of the system, pathogenicity, immunological and toxicity concerns, and the like. It is clear that there is no single viral system that is suitable for all applications. When selecting a viral delivery system to use in the present invention, it is important to choose a system where RNAi expression construct-containing viral particles is: 1) reproducibly and stably propagated; 2) able to be purified to high titers; and 3) able to mediate targeted delivery (delivery of the multiple-promoter RNAi expression construct to the target tissue (e.g., cardiomyocytes) without widespread dissemination).

In addition, hybrid viral systems may be used to combine useful properties of two or more viral systems. For example, the site-specific integration machinery of wild-type AAV may be coupled with the efficient internalization and nuclear targeting properties of adenovirus. AAV in the presence of adenovirus or herpesvirus undergoes a productive replication cycle; however, in the absence of helper functions, the AAV genome integrates into a specific site on chromosome 19. Integration of the AAV genome requires expression of the AAV rep protein. As conventional rAAV vectors are deleted for all viral genes including rep, they are not able to specifically integrate into chromosome 19. However, this feature may be exploited in an appropriate hybrid system. In addition, non-viral genetic elements may be used to achieve desired properties in a viral delivery system, such as genetic elements that allow for site-specific recombination.

The RNAi expression construct is packaged into viral particles. Any method known in the art may be used to produce infectious viral particles whose genome comprises a copy of the viral RNAi expression construct. The packaging cell line may be any cell line that is capable of expressing viral proteins, including but not limited to 293, HeLa, A549, PerC6, D17, MDCK, BHK, Cf2Th, or any other line known to or developed by those skilled in the art. One packaging cell line is described, for example, in U.S. Pat. No. 6,218,181, incorporated herein by reference.

Alternatively, a cell line that does not stably express necessary viral proteins may be co-transfected with two or more constructs to achieve efficient production of functional particles. One of the constructs comprises the viral RNAi expression cassette, and the other plasmid(s) comprises nucleic acids encoding the proteins necessary to allow the cells to produce functional virus (replication and packaging construct) as well as other helper functions.

The packaging cell line or replication and packaging construct may not express envelope gene products. In such an embodiment, the gene encoding the envelope gene can be provided on a separate construct that is co-transfected with the viral RNAi expression construct. As the envelope protein is responsible, in part, for the host range of the viral particles, the viruses may be pseudotyped. A "pseudotyped" virus is a viral particle having an envelope protein that is from a virus other than the virus from which the genome is derived. One of skill in the art can choose an appropriate pseudotype for the viral delivery system used and cell to be targeted. In addition to conferring a specific host range, a chosen pseudotype may permit the virus to be concentrated to a very high titer. Viruses alternatively can be pseudotyped with ecotropic envelope proteins that limit infection to a specific species (e.g., ecotropic envelopes allow infection of, for example, murine cells only, where amphotropic envelopes allow infection of, e.g., both human and murine cells). In addition, genetically-modified ligands may be used for cell-specific targeting, such as the asialoglycoprotein for hepatocytes, or transferrin for receptor-mediated binding.

After production in a packaging cell line, the viral particles containing the RNAi expression cassettes are purified and quantified (titered). Purification strategies include, but are not limited to, density gradient centrifugation or column chromatographic methods.

The RNAi or RNAi expression cassette disclosed herein may be introduced to cardiomyocytes by application to the heart via, but not limited to, injection or perfusion.

In one embodiment, an RNAi expression cassette may be introduced into the target cells in vitro or ex vivo and then subsequently placed into an animal to affect therapy, or administered directly to an organism, organ or cell by in vivo administration. Delivery by viral infection may be one method of delivery. The vectors comprising the cassettes may be administered to a mammalian host using any convenient protocol, where a number of different such protocols are known in the art.

The AAV vectors can be formulated into preparations for injection or administration by dissolving, suspending or emulsifying them in appropriate, pharmaceutically acceptable carriers or diluents. Examples of such pharmaceutically acceptable carriers or diluents include an aqueous or non-aqueous solvent, such as oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In one embodiment, a pharmaceutical composition is disclosed including, a recombinant adeno-associated virus (AAV) vector and a pharmaceutically acceptable carrier, where the vector includes an RNAi expression cassette whose RNA expression product leads to a decrease in expression of phospholamban (PLB) mRNA and a decrease in the amount of PLB protein in the cell, and where the RNA expression product of the RNAi expression cassette includes a nucleotide sequence that hybridizes under stringent conditions to a nucleotide sequence of the PLB gene mRNA.

In one aspect, the RNAi expression cassette includes the nucleotide sequence 5' GGATCCCGTACCT-TACTCGCTCGGCTATTCAAGAGATAGC-CGAGCGAGTAAGGTA TTTTTTGGAAAAGCTT 3'(SEQ ID NO:1). In another aspect, the RNA expression product includes the target sequence 5' UACCUUACUCGCUCG-GCUA 3' (SEQ ID NO:2).

In yet another aspect, the present invention contemplates a pharmaceutical composition including an RNAi expression construct where the RNAi construct includes one or more RNAi expression cassettes each comprising a RNAi targeting sequence including a nucleotide sequence which is at least 70% identical to at least part of a nucleotide sequence including PLB or a derivative, ortholog or homolog thereof.

The methods and compositions of the invention involve the administration of an effective amount of the RNAi or RNAi cassette so as to achieve the intended or desired result in modulation of gene expression. This is generally measured phenotypically. It is envisaged that, in some cases, some degree of routine trial and error, as is well known in the pharmaceutical arts, may be necessary in order to determine the most effective amount to be administered.

Reference herein to "genetic therapy" includes gene therapy. The genetic therapy contemplated by the present invention further includes somatic gene therapy whereby cells are removed, genetically modified and then replaced into an individual. The gene therapy may be transient or permanent. Preferably, the animal is a human.

In another aspect, the present invention further extends to genetically modified cells comprising a ddRNAi expression cassette as described herein, or a genomically integrated form or part thereof. In one aspect, the cell is a mammalian cell. In a related aspect, the cell is a primate or rodent cell, and may include a human or mouse cell.

Also disclosed are pharmaceutical kits containing the AAV vector in a suitable pharmaceutical suspension for administration. In this aspect, the invention provides a pharmaceutical kit for delivery of said recombinant adeno-associated viral vector or virion. The kit may contain a container for administration of a predetermined dose. The kit further may contain a suspension containing the gene transfer vector or virion for delivery of a predetermined dose, said suspension comprising (a) the AAV gene transfer vector or virion comprising an RNAi expression cassette (b) a physiologically compatible carrier.

The invention also provides RNAi expression cassettes that encode the RNA molecule(s) capable of forming a double-stranded RNA complex and thus capable of inducing RNA interference. Such RNAi expression cassettes may be a single DNA molecule as part of a rAAV genome which, when introduced into a cell, gives rise to a single RNA molecule capable of forming intramolecularly a dsRNA complex. However it will be understood from the following description that more than one rAAV genome or RNAi expression cassette or RNA coding region may be introduced into a cell, either simultaneously or sequentially, to give rise to two or more RNA molecules capable of forming intermolecularly a dsRNA complex. Typically, the two RNA moieties capable of forming a dsRNA complex, whether intra-or intermolecularly, are at least in part sense and at least in part antisense sequences of a gene or nucleic acid sequence whose expression is to be down-regulated or decreased.

The design of the RNAi expression cassette does not limit the scope of the invention. Different strategies to design an RNAi expression cassette can be applied, and RNAi expression cassettes based on different designs will be able to induce RNA interference in vivo. Features common to all RNAi expression cassettes are that they comprise an RNA coding region which encodes an RNA molecule which is capable of inducing RNA interference either alone or in combination with another RNA molecule by forming a double-stranded RNA complex either intramolecularly or intermolecularly.

Different design principles can be used to achieve that same goal and are known to those of skill in the art. For example, the RNAi expression cassette may encode one or more RNA molecules. After or during RNA expression from the RNAi expression cassette, a double-stranded RNA complex may be formed by either a single, self-complementary RNA molecule or two complementary RNA molecules. Formation of the dsRNA complex may be initiated either inside or outside the nucleus.

In one aspect there is provided a double-stranded RNA complex, which comprises, a first RNA portion capable of hybridizing under physiological conditions to at least a portion of an mRNA molecule, and a second RNA portion wherein at least a part of the second RNA portion is capable of hybridizing under physiological conditions to the first portion. In one aspect, the first and second portions are part of the same RNA molecule and are capable of hybridization at physiological conditions, such as those existing within a cell, and upon hybridization the first and second portions form a double-stranded RNA complex.

In another aspect, there is provided a linear RNA molecule for forming a double-stranded RNA complex, which RNA comprises a first portion capable of hybridizing to at least a portion of an mRNA molecule within a cell and a second portion wherein at least part of the second portion is capable of hybridizing to the first portion to form a hairpin dsRNA complex.

In yet another aspect, the method comprises AAV-mediated expression of RNA with partial or fully double-stranded character in vivo.

In certain embodiments the invention may employ ribozyme-containing RNA molecules to generate dsRNA complexes, thereby overcoming certain known difficulties associated with generating dsRNA. For example, the ribozyme functionality might be used to remove polyadenylation signals, thus preventing or minimizing release of the RNA molecule from the nucleus of a cell. In other embodiments the invention is based on the ability of a portion of the RNA molecule to encode an RNA or protein that enhances specific activity of dsRNA. One example of this specific activity-enhancing portion of the RNA molecule is a portion of the molecule encoding the HIV Tat protein to inhibit the cellular breakdown of dsRNA complexes.

This invention also provides a method of treating heart failure in a subject, or decreasing ventricular arrhythmias, or increasing survival or a subject after heart failure by inhibiting the expression of PLB in the subject's heart, comprising administering to the subject a therapeutically effective amount of a pharmaceutical composition comprising rAAV virions comprising one or more RNAi expression cassettes encoding at least one RNA molecule which is capable of forming a dsRNA complex where, under hybridizing conditions, the a portion of the dsRNA complex is able to hybridize to at least a portion of an mRNA encoded by a PLB gene.

In another embodiment, a method of increasing calcium uptake into the sarcoplasmic reticulum (SR) is disclosed including, contacting a muscle tissue sample with an adeno-associated virus (AAV) vector, where the vector includes a polynucleotide sequence encoding an RNAi expression product, where the RNAi includes a nucleotide sequence that hybridizes under stringent conditions to a nucleotide sequence of the PLB target gene mRNA, thereby increasing calcium uptake in the SR.

For purposes of this invention, by "mammalian subject" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, hamsters, rabbits and guinea pigs, and the like. The term does not denote a particular age or sex. Thus, adult and newborn subjects, as well as fetuses, whether male or female, are intended to be covered.

For purposes of this invention, the terms "individual" or "subject" or "patient" as used herein refer to vertebrates, particularly members of the mammalian species and include, but are not limited to, domestic animals, sports animals, primates and humans; more particularly the term refer to humans.

The virions of the present invention may be suspended in a pharmaceutically acceptable delivery vehicle (i.e., physiologically compatible carrier), for administration to a human or non-human mammalian patient. Suitable carriers may be readily selected by one of skill in the art and may depend on the nature of the nucleic acid transfer vector chosen. Pharmaceutical compositions will comprise sufficient genetic material to produce a therapeutically effective amount of dsRNA complexes. The pharmaceutical compositions will also contain a pharmaceutically acceptable excipient. Such excipients include any pharmaceutical agent that does not itself induce an immune response harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. Other exemplary carriers include lactose, sucrose, calcium phosphate, gelatin, dextran, agar, pectin, peanut oil, sesame oil, and water. The selection of the carrier is not a limitation of the present invention. Optionally, the compositions of the invention may contain, in addition to the AAV virions and carrier(s), other conventional pharmaceutical ingredients, such as preservatives, or chemical stabilizers. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin and albumin. A thorough discussion of pharmaceutically acceptable excipients is available in REMINGTON'S PHARMACEUTICAL SCIENCES (Mack Pub. Co., N.J. 1991).

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

In this invention, administering the instant pharmaceutical composition can be effected or performed using any of the various methods and delivery systems known to those skilled in the art. The administering can be performed, for example, intravenously, orally, via implant, transmucosally, transdermally, intramuscularly, and subcutaneously. The compositions may be suitable for intravenous administration, intra-arterial administration, intraventricular administration, or heart valve perfusion. In addition, the instant pharmaceutical compositions ideally contain one or more routinely used pharmaceutically acceptable carriers. Such carriers are well known to those skilled in the art. The following delivery systems, which employ a number of routinely used carriers, are only representative of the many embodiments envisioned for administering the instant composition.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Determining a therapeutically or prophylactically effective amount of the instant pharmaceutical composition can be done based on animal data using routine computational methods. Appropriate doses will depend, among other factors, on the specifics of the transfer vector chosen, on the route of administration, on the mammal being treated (e.g., human or non-human primate or other mammal), age, weight, and general condition of the subject to be treated, the severity of the disorder being treated, the location of the area within the heart being treated and the mode of administration. Thus, the appropriate dosage may vary from patient to patient. An appropriate effective amount can be readily determined by one of skill in the art.

A therapeutically effective human dosage for in vivo delivery of said vector according to the present invention is believed to be in the range of from about 20 to about 50 ml of saline solution containing concentrations of from about $10^{10}$ to $10^{14}$ functional vector/ml solution. The dosage will be adjusted to balance the therapeutic benefit against any side effects. In yet another embodiment, pharmaceutically effective dose of the AAV is generally in the range of concentrations of from about $1\times10^5$ to $1\times10^{50}$ genomes rAAV, about $10^8$ to $10^{2o}$ genomes AAV, about $10^{10}$ to about $10^{16}$ genomes, or about $10^{11}$ to $10^{16}$ genomes AAV. A human dosage may be about $1\times10^{13}$ AAV genomes AAV. Such concentrations may be delivered in about 0.001 ml to 100 ml, 0.05 to 50 ml, or 10 to 25 ml of a carrier solution. Other effective dosages can be readily established by one of ordinary skill in the art through routine trials establishing dose response curves.

Dosage treatment may be a single dose schedule or a multiple dose schedule. Moreover, the subject may be administered as many doses as appropriate. One of skill in the art can readily determine an appropriate number of doses. However, the dosage may need to be adjusted to take into consideration an alternative route of administration, or balance the therapeutic benefit against any side effects. Such dosages may vary depending upon the therapeutic application for which the recombinant vector is employed.

The vector particles are administered in sufficient amounts to enter the desired cells and to guarantee sufficient levels of functionality of the transferred nucleic acid composition to provide a therapeutic benefit without undue adverse, or with medically acceptable, physiological effects which can be determined by those skilled in the medical arts.

Optionally, in specific embodiments, AAV-mediated delivery according to the invention may be combined with delivery by other viral and non-viral vectors. Such other viral vectors including, without limitation, adenoviral vectors, retroviral vectors, lentiviral vectors. herpes simplex virus (HSV) vectors, and baculovirus vectors may be readily selected and generated according to methods known in the art. Similarly, non-viral vectors, including, without limitation, liposomes, lipid-based vectors, polyplex vectors, molecular conjugates, polyamines and polycation vectors, may be readily selected and generated according to methods known in the art. When administered by these alternative routes, the dosage is desirable in the range described above.

Animals (including humans) possess a natural defense mechanism against pathogens with dsRNA genomes: The presence of dsRNA in the cytosol induces the activation of Interferon-related pathways, which suppress RNA interference. Thus, in order to avoid the activation of those pathways, the dsRNA complex should not exceed 30 base pairs in length—the prime rule in designing siRNA constructs.

In certain embodiments, the length of the dsRNA complex is at least 20, 21 or 22 base pairs in length, e.g., corresponding in size to RNA products produced by Dicer-dependent cleavage.

The following examples are intended to illustrate but not limit the invention.

EXAMPLE 1

Materials and Methods

Development of Recombinant Adenoviral and AAV Vectors

Figure 1A:
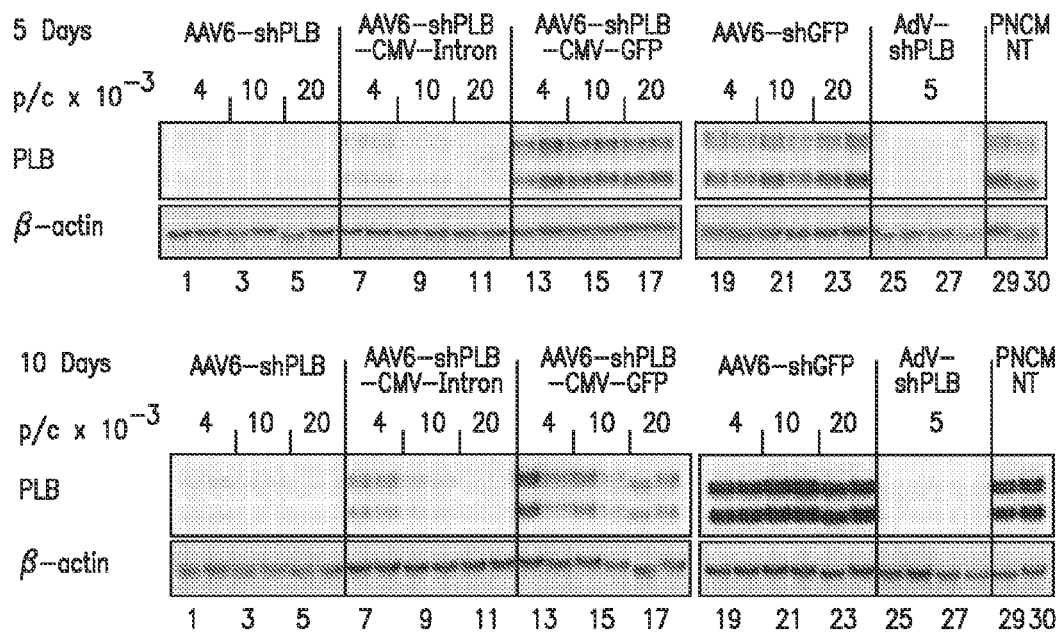
FIG. 1A is a pictorial diagram showing panels of Northern blots demonstrating targeted silencing by different vectors in the development of RNA interference (RNAi) vectors for heart failure (HF) therapy. Shown is a comparison of the target silencing efficacy of shRNA expression vectors in primary neonatal rat cardiomyocytes (PNCMs). Cells were harvested 5 days (upper part) or 10 days (lower part), respectively, after treatment with the respective vector at the dose in particles per cell (p/c) given above the lanes. Northern blots were then carried out using a rat PLB-specific probe. To confirm equal RNA loading the blots were striped and rehybridized with a β-actin-specific probe. Lanes 1 to 18 show dose dependency of RNAi-mediated PLB-mRNA downregulation for the adeno-associated virus (AAV)-based vectors AAV-shPLB (lane 1-6), AAV-shPLB-CMV-β-intron (lane 7-12), and AAV-shPLB-CMV-GFP (lane 13-18). Lanes 19-24 show a control for unspecific shRNA effects PLB-mRNA expression after treatment with AAV-shGFP, which generates an shRNA sequence targeting green fluorescent protein (GFP) (lanes 19-24). For comparison with AAV the adenoviral vector AdV-shPLB (lanes 25-28) was used. PLB-mRNA was ≧98% ablated until day 10 by rAAV-shPLB at the lowest dose of $4 \times 10^3$ p/c (lanes 1,2), similar to AdV-shPLB (lanes 25-28). Incorporation of a CMV-GFP expression cassette in the rAAV-shPLB vector (lanes 7-12) to provide this vector with a tag which is easily detectable by in vivo imaging, led to strong GFP expression in infected cells (not shown) but unexpectedly abolished its PLB gene silencing effect. Incorporation of a CMV-β-intron cassette (lanes 12-18) had a similar but less pronounced effect.
Figure 1B:
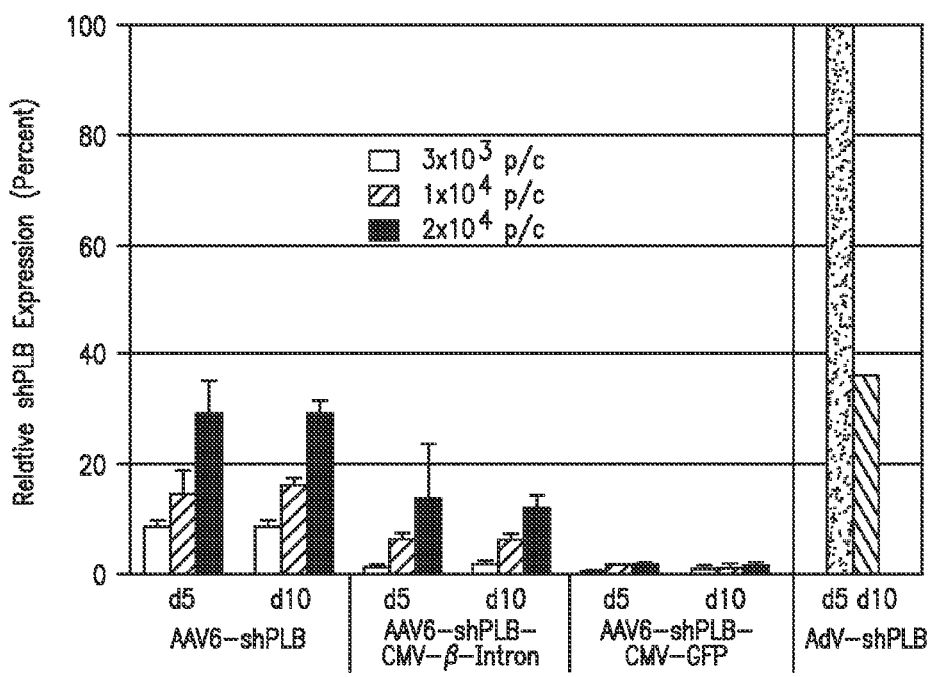
FIG. 1B is a graphical diagram showing the cellular shRNA levels produced by the vectors from FIG. 1A. In the presence of a CMV-GFP cassette shPLB production was abolished (lanes 13-18), whereas the U6-shPLB vector without additional sequences showed stable expression over 5 (lanes 1-3) and 10 days (lanes 4-6). AdVshPLB generated very high shPLB levels on day 5 which then declined rather rapidly in NRCMs.
Figure 1C:
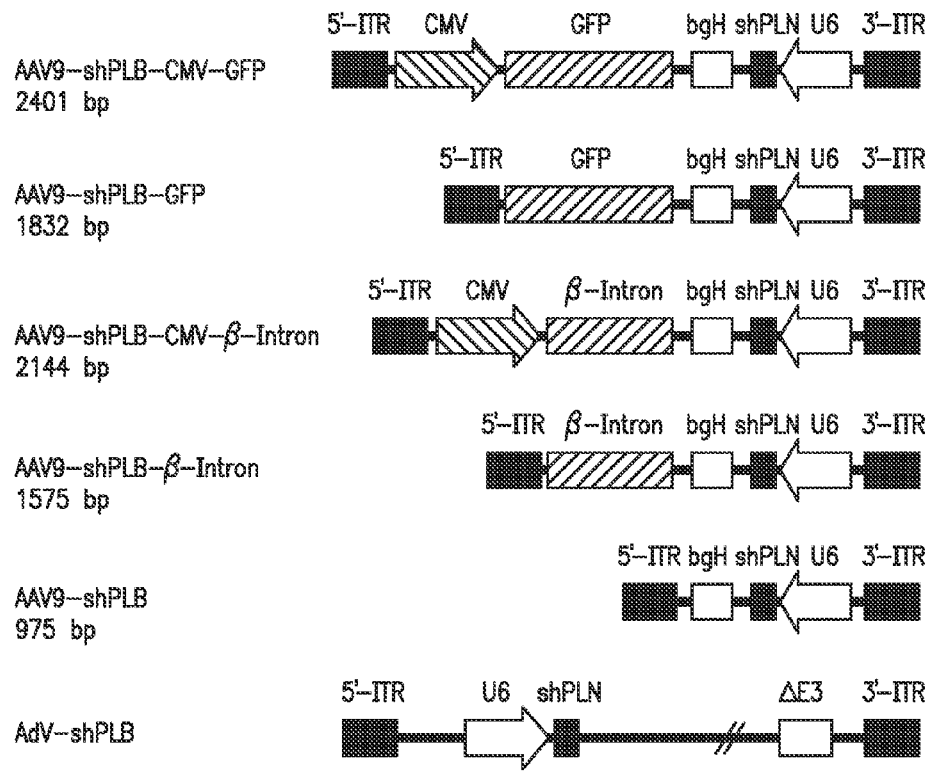
FIG. 1C is a pictorial diagram showing detailed maps of adenoviral and AAV vectors. AAV-shPLB has the same U6-shRNA expression system as AdV-shPLB and their corresponding shGFP control vectors. In addition, four CMV-containing vectors carry cassettes with CMV-GFP or CMV-β-intron cassettes in head-to-head orientation with the U6-shRNA sequence and separated from them by a bovine growth hormone (bgH) terminal signal.

Recombinant adeno-associated virus (rAAV) vectors were developed for the in vitro studies as pseudotyped rAAV2.6 and for the in vivo work as rAAV2.9. Both contained identical AAV2 vector genomes with the indicated shRNA expression cassettes and were processed identically with the exception of using the plasmid AAV6cap for rAAV2.6 and AAV9cap for rAAV2.9, respectively. Throughout all in vitro and in vivo studies only self-complementary ("dimeric") rAAV genomes were used due to their enhanced performance as compared to single-stranded ("monomeric") rAAV vectors. Starting from an shRNA expression cassette previously used in an adenoviral (AdV) vector AdV-shPLB, which efficiently and stably silenced PLB expression in cultured primary neonatal rat cardiomyocytes (PNCMs), AdV and rAAV vectors co-expressing shRNA and GFP as a marker was sought to be developed which would allow vector tracking during the experiment with heart failure (HF) animals by in vivo imaging. However, a construct, rAAV-shPLB-CMV-GFP displayed very low silencing activity as compared to the original AdV-shPLB vector which contained no CMV-GFP component (FIG. 1A). The rAAV vector produced GFP under CMV control with transcription in the CMV-GFP cassette running opposite to the U6-promotor-shRNA cassette. To test if the CMV promoter itself and/or the GFP sequence were responsible for the loss of silencing activity, the vector rAAV-shPLB-CMV-β-intron was constructed with an intronic "stuffer" sequence instead of the GFP. Both rAAV-shPLB- CMV-GFP (size 2.30 kb) and rAAV-shPLB-CMV-β-intron (size 2.55 kb) had sizes considered necessary for packaging in the capsid. A third vector which contained neither CMV nor GFP or β-intron, but only the original U6-shPLB cassette from AdV-PLB, rendering at total vector genome size of 1.15 kb. Nevertheless this "minimalistic" rAAV-shPLB was efficiently packaged during the standard procedure, probably as concatemer. Vector maps are shown in FIG. 1C.

Virus Vector Production and Purification rAAV9-shGFP and rAAV9-shPLB were produced using the two-plasmids protocol described by Zolotukin et al. (*Gen Ther* (1999) 6(6):973-985), with the following modifications. 293-T cells (ATCC, Manassas, Va.) were grown in triple flasks for 24 h (DMEM, 10% FBS) prior to adding the calcium phosphate precipitate. After 72 hours, the virus was purified from benzonase-treated cell crude lysates over an iodixanol density gradient (Optiprep, Greiner Bio-One Inc., Longwood, Fla.), followed by heparin-agarose type I affinity chromatography (Sigma-Aldrich Inc., St. Louis, Mo.). Finally viruses were concentrated and formulated into lactated Ringer's solution (Baxter Healthcare Corporation, Deerfield, Ill.) using a Vivaspin 20 Centrifugal concentrators 50K MWCO (Vivascience Inc., Carlsbad, Calif.), and stored at −80° C.

Vector Quality Assessment and Titration

Vector stock biochemical purity (>95%) was assessed by silver staining after electrophoresis. Genome containing particles (gcp) were determined by a real-time PCR approach (LightCycler, Roche Diagnostics) using the SYBR™ GREEN TAQ READYMIX™ (SIGMA, Saint-Louis, Mo.) and primers CMV-F and CMV-R.

Vector Evaluation in Cardiomyocyte Cultures

Primary neonatal cardiomycytes (NRCMs) are suitable to pre-test any RNAi-based cardiac therapy before its definitive test in vivo since, although developmentally regulated, the SERCA2a/PLB system functions well in NRCMs and adenoviral gene transfer strategies targeting the SERCA2a/PLB system were successful in both neonatal and adult cardiomyocytes. Although both cell types are well suited for in vitro pre-testing, a number of other differences between cultured cardiomyocytes and the intact heart in vivo render any in vitro study of RNA-based therapies in cultured cells rather preliminary.

Cell cultures: Primary cardiomyocytes (PNCMs) and primary neonatal cardiomyocytes (NRCMs) were prepared from ventricular tissue of 1-3 day-old Wistar rat pups. PNCMs were grown in 6-well dishes.

Evaluation of phospholamban silencing: PLB, Tn1, NCX, and SERCA2a mRNA and protein expression levels in NRCMs and rat hearts, as well as SERCA2a and NCX protein in rat hearts, were determined by Northern blot analysis as described (Fechner et al., *Gene Therapy* (2006); in press).

Calcium Transients During RNAi Treatment: $[Ca^{2+}]_i$ transients were measured during electrical stimulation at 1 Hz after loading of NRCMs with 8 µM Fluo-4/AM for 20 min (image capture at 120 Hz, 8.3 ms per image). Five treatment groups of NRCMs (number of cells) were studied: AAV9-shPLB (n=26), AAV9-shGFP (n=26), AdV-shPLB (n=71), AdV-shGFP (n=49), and untreated control cells (n=32). The amplitude of the transient (systolic $[Ca^{2+}](F/F_0)$), its time to peak (TTP) (ms), and the time constant τ of its decay (ms) were measured. The measurement of $[Ca^{2+}]_i$ transients during AAV9-shPLB treatment of NRCMs (FIGS. 1E and 1F) showed that this vector led to significantly higher amplitude and accelerated transient kinetics (with shortened TTP and t) compared to the AAV9-shGFP group with transients indistinguishable from untreated cells. AdV-shPLB treatment also resulted in a significantly higher amplitude compared to the AdV-shGFP group. In contrast to the AAV9 groups, however, the TTP was prolonged in AdV-shPLB vs. AdV-shGFP and there was no difference in t. Therefore additional studies of sarcoplasmic reticulum (SR) $Ca^{2+}$ loading in the AdV groups (FIG. 1D) were performed as follows: $[Ca^{2+}]_i$ transients were again measured during electrical stimulation at 1 Hz after loading of NRCMs with 8 µM Fluo-4/AM for 20 min, but followed by rapid addition of 20 mM caffeine which blocks re-uptake of $Ca^{2+}$ into the SR via SERCA2a. Electrically stimulated $[Ca^{2+}]_i$ transients were compared with the caffeine-induced and the fractional release of $Ca^{2+}$ was calculated (see Kockskämper, et al. Endothelin-1 enhances nuclear Ca2+ transients in atrial myocytes through Ins(1,4,5)P3-dependent Ca2+ release from perinuclear Ca2+ stores. *Journal of Cell Science*. 2008; 121:186-195, and references cited therein).

Induction of hypertrophy: Phenylephrine (PE) at a concentration of 100 µM, angiotensin II (Ang-ID at 10 µM, and endothelin-1 (ET-1) at 100 nM were employed in part of the in vitro studies as hypertrophic stimuli. TAQMAN™ assays to quantitate the cellular miRs were performed in PNCMs/NRCMs under baseline conditions (FIG. 4A) or in the presence of either hypertrophic agent (FIGS. 4B-4D). The agent was added on day 2 of culture, either alone or together with the respective RNAi vector. small RNA assays: short hairpin RNA (shRNA) expression levels were determined by TAQMAN™ assays using the following primers. In a search for possible vector dose-dependent influences of vector-derived shRNAs on cardiac cellular miRNA pathways, TAQMAN™ assays were employed to quantitate the following miRs known to be expressed in the heart: miRNA-1, miRNA-24, miRNA-133a, miRNA-208, and miRNA-195.

Quantitation of Gene Expression and shRNA Production by Taqman Assays microRNA assays: In a search for possible influences of vector-derived shRNAs on cardiomyocyte miRNAs TAQMAN™ assays were used to quantitate (FIGS. 4A-4C) two miRNAs (miRNA-1, miRNA-133a) known to be functionally expressed in the heart. BNP assay: Cardiac BNP gene expression was likewise quantitated by TAQMAN™ in the hearts of vector-treated rats (FIG. 3G). shPLB production: The quantitation of short hairpin RNA transcription by the different RNAi vectors (FIG. 1B) followed a previously published protocol (Fechner, et al. Highly Efficient and Specific Modulation of Cardiac Calcium Homeostasis by Adenovector-Derived short hairpin RNA Targeting Phospholamban. *Gene Therapy*. 2007; 14:211-218; and Fechner, et al. Coxsackievirus B3 and adenovirus infections of cardiac cells are efficiently inhibited by vector-mediated RNA interference targeting their common receptor. *Gene Ther*. June 2007; 14(12): 960-971).

Transaortic Banding

Four-week old Sprague Dawley rats (70-80 g) were anesthetized with intraperitoneal pentobarbital (65 mg/kg) and placed on a ventilator. A suprasternal incision was made exposing the aortic root and a tantalum clip with an internal diameter of 0.58 mm (Week, Inc.) was placed on the ascending aorta. Animals in the sham group underwent a similar procedure without insertion of a clip. The supraclavicular incision was then closed and the rats were transferred back to their cages. The supraclavicular approach was performed because during gene delivery a thoracotomy is necessary and by not opening the thorax during the initial aortic banding, avoids adhesions when gene delivery is performed.

Animals were initially divided into two groups: one group of 56 animals with aortic banding and a second group of 12 animals which were sham-operated (10 of the sham operated animals survived). In the animals which were aortic banded we waited 25-30 weeks for the animals to develop left ventricular dilatation and a decrease in ejection fraction by 25% prior to cardiac gene transfer. From the initial 56 who underwent pressure overload hypertrophy only 40 animals survived and were further divided to receive either Ad-shGFP (n=10) or Ad-shPLB (n=10), or AAV9-shGFP (n=10) or AAV9-shPLB (n=10).

Serial Echocardiographic Assessment

After twenty-two weeks of banding, serial echocardiograms were performed on a weekly basis in lightly anesthetized animals (pentobarbital 40 mg/kg intra-peritoneally). Transthoracic M-mode and two-dimensional echocardiography was performed with a GE Vivid-7 Ultrasound machine and a 12 MHz broadband transducer. A mid-papillary level left ventricular short axis view was used and measurements of posterior wall thickness, left ventricular diastolic dimension and fractional shortening were collected. Gene transfer was performed in all animals within 3 days of detection of a drop in fractional shortening (FS) of >25% compared to FS at 12 weeks post-banding. In the sham operated rats, gene delivery was performed at 27 weeks.

Cardiac Distribution of AAV9 Vectors after Intravenous Injection

Rats were injected intravenously (i.v.) either with a vector rAAV9-GFP which expresses the marker protein GFP, or with saline. One month following delivery of rAAV9-GFP or saline, the hearts were removed and visualized under a fluorescent system (Maestro In Vivo Imaging, Woburn, Mass.) at 510 nm with single excitation peak at 490 nm of blue light (FIGS. 2B and 2C) shows the images observed.

Figure 2A:
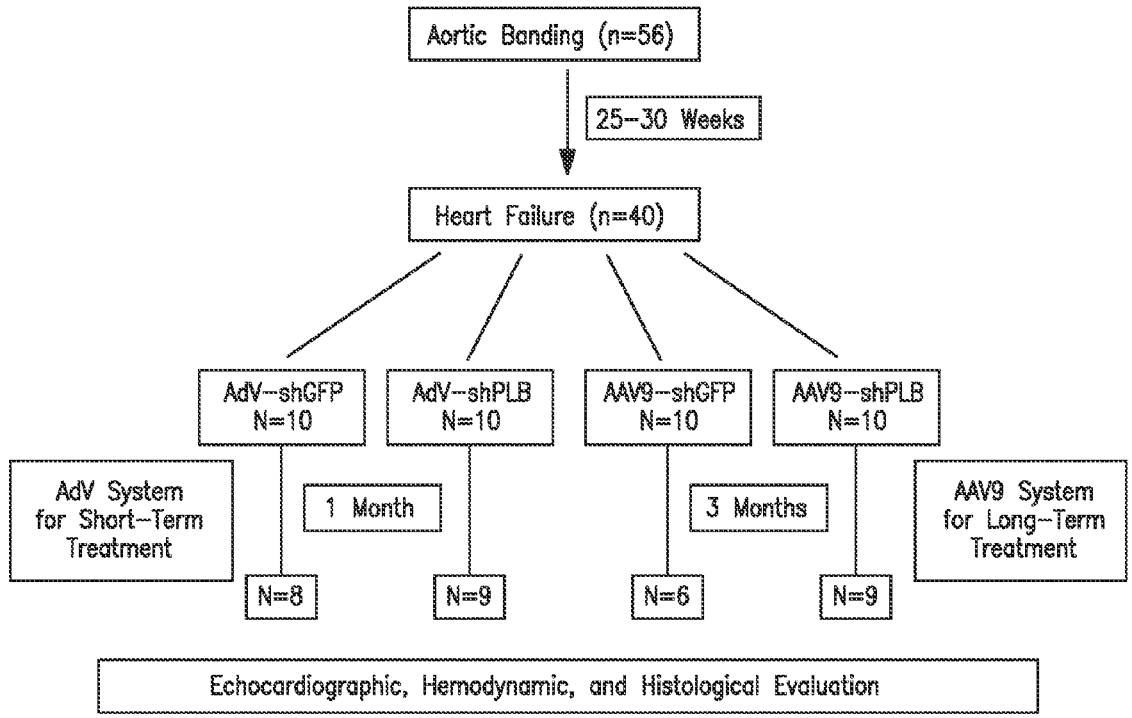
FIG. 2A is a flow diagram illustrating the protocol for RNAi therapy of HF in vivo. Animals used for in vivo RNAi therapy were initially divided in two groups: one group of 56 animals with aortic banding (TAB) and a second of 12 which were sham-operated. In the TAB animals 25-30 weeks passed to allow them to develop left ventricular (LV) dilatation and a decrease in fraction shortening (FS) by 25%, as assessed by serial echocardiography, prior to cardiac RNAi vectors transfer. From the initial 56 who underwent TAB, 40 animals survived and were further divided to receive either Ad-shGFP (n=10) or Ad-shPLB (n=10), or the control vectors AAV9-shGFP (n=10) or AAV9-shPLB (n=10). Vector injection was as carried out via 22 G catheter containing 200 μl of adenoviral ($3\times10^{10}$ pfu) or AAV9 ($5\times10^{11}$ vector genomes) vector solution. The catheter was advanced from the LV apex to the aortic root, aorta and main pulmonary artery were clamped for 40 sec distal to the catheter site and the solution injected. Outcome evaluation by echocardiography, tip catheter, morphometry, and histology was after one month in the adenoviral vector groups and after three months in the AAV vector treatment groups (see, FIGS. 3A-3F). In the AdV groups 8/10 and 9/10 animals survived after 1 month. After 3 months 9/10 survived in the rAAV-shPLB and 6/10 in the rAAV-shGFP group. Further studies on cardiac expressed microRNAs in these groups were conducted at the same times.
Figure 2B:
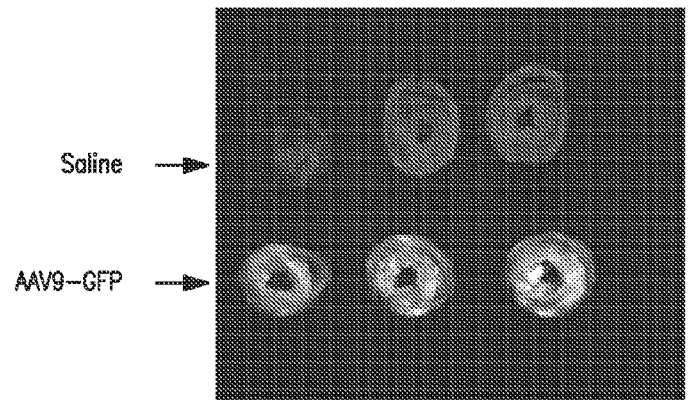
FIG. 2B is a pictorial diagram showing the hearts of rats that were injected i.v. with an rAAV9-GFP vector expressing green florescent protein (lower), or with saline (upper). One month after injection, the hearts were removed and visualized by GFP imaging which showed a grossly homogeneous signal in cardiac cross sections in the rAAV9-GFP group, and no signal in the saline group.
Figure 2C:
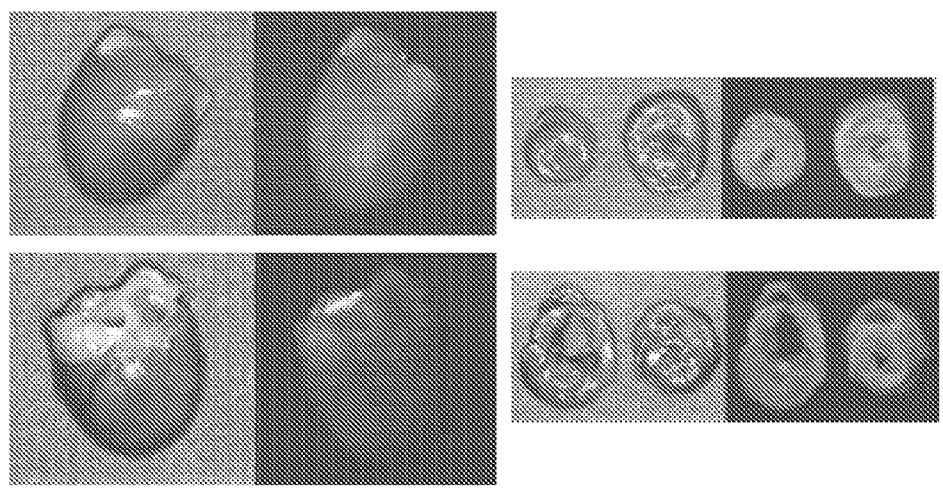
FIG. 2C is a pictorial diagram showing an overview on GFP fluorescence from hearts from rAAV9-GFP-treated rats reaching 90% of surface area at one month.
Figure 2D:
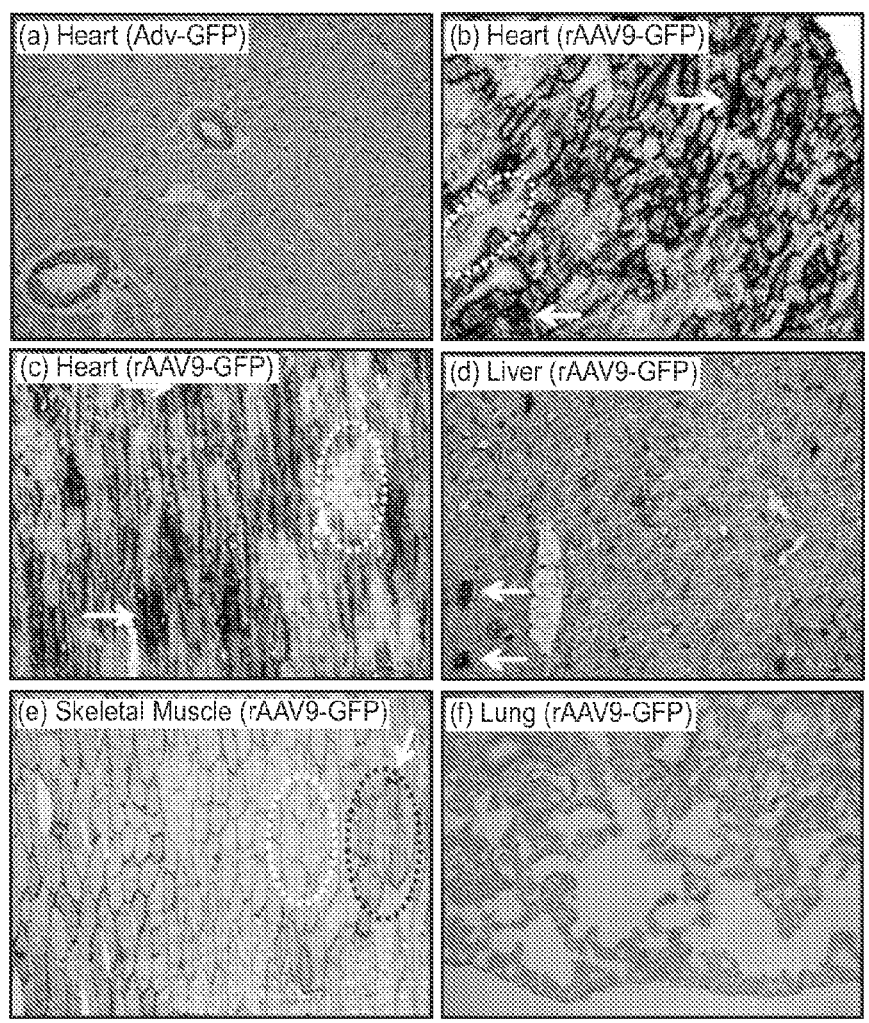
FIG. 2D is a pictorial diagram showing immunhistochemical staining of GFP in different organs one month after i.v. injection of rAAV9-GFP into rats. Whereas after i.v. injection of an adenoviral vector (AdV-GFP) no GFP was detected in the heart (a), rAAV9-GFP treatment resulted in strong GFP expression (b) and (c) which was grossly homogeneous. Few areas are completely devoid of GFP immunoreactivity (encircled), others show homogeneous cytoplasmic staining (encircled). Staining is particularly dense at sites where high expression over one month has obviously resulted in the formation of precipitates (arrows) of GFP which is stable in cells, in contrast to shRNA generated from RNAi vectors. An average of 70% of cardiomyocytes were positive by immunohistochemistry, with variability of expression among individual cells. (e) shows skeletal muscle with faint staining of a fraction of cells, whereas the liver shows prominent signal of individual cells only (d). No signal was visible in the lungs. Further data on AAV9 distribution are given in FIG. 2J with GFP quantitation by Western blot analyses, documenting highest affinity of rAAV9-GFP expression for the heart. Liver and skeletal muscle showed low and the lungs only very faint expression.
Figure 2E:
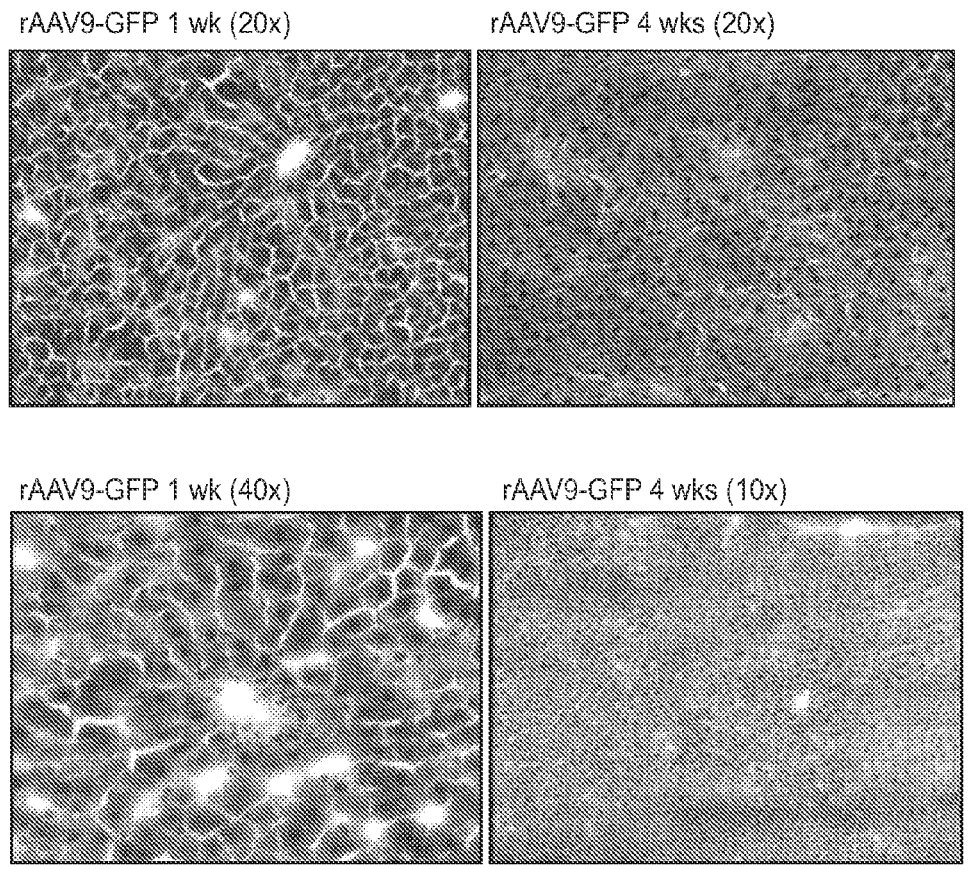
FIG. 2E is a pictorial diagram showing the haematoxylin-eosin staining of livers 1 week and 4 weeks after i.v. injection of rAAV9-GFP shows no evidence of toxicity. rAAV-shRNA vector also resulted in no hepatotoxicity.
Figure 2F:
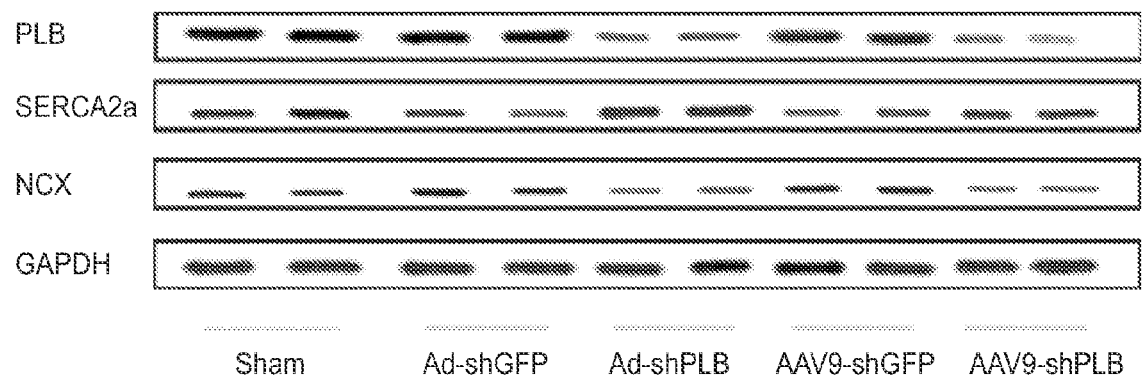
FIG. 2F is a pictorial diagram showing panels of Northern blots demonstrating a significant decrease of cardiac PLB protein after 1 month of AdV-shPLB and 3 months of rAAV9-shPLB therapy compared to the shGFP control groups. The NCX and GAPDH protein remained unchanged. SERCA2a was decreased in the shGFP groups which were in heart failure as compared to sham, whereas SERCA2a was significantly increased in both shPLB groups.
Figure 2G:
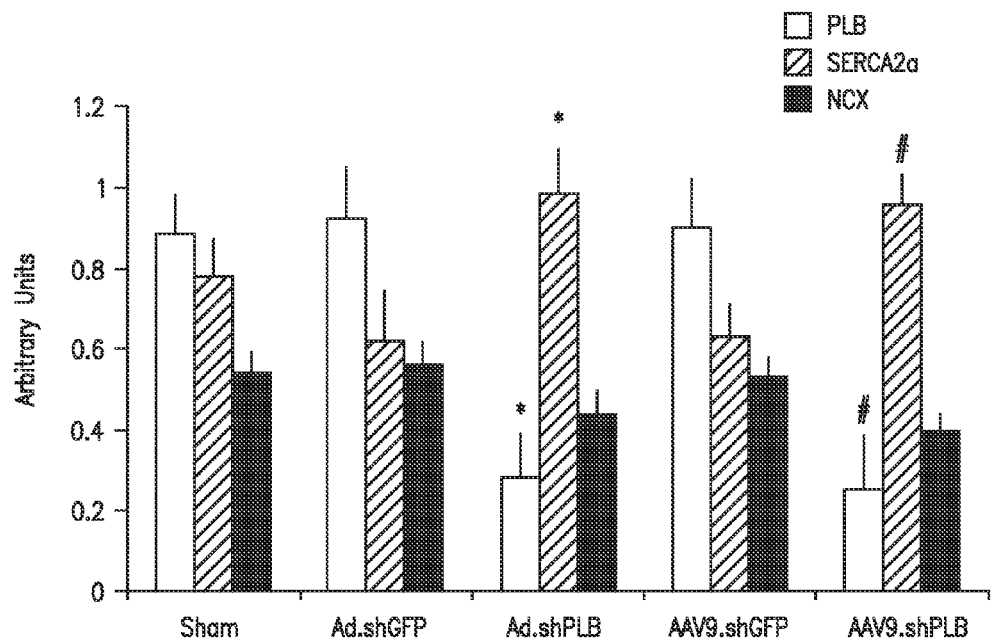
FIG. 2G is a graphical diagram showing a statistical evaluation of Western blots from the different treatment groups. * denotes $p<0.05$ compared to AdV-shGFP, # $p<0.05$ compared to rAAV9-shGFP.
Figure 2H:
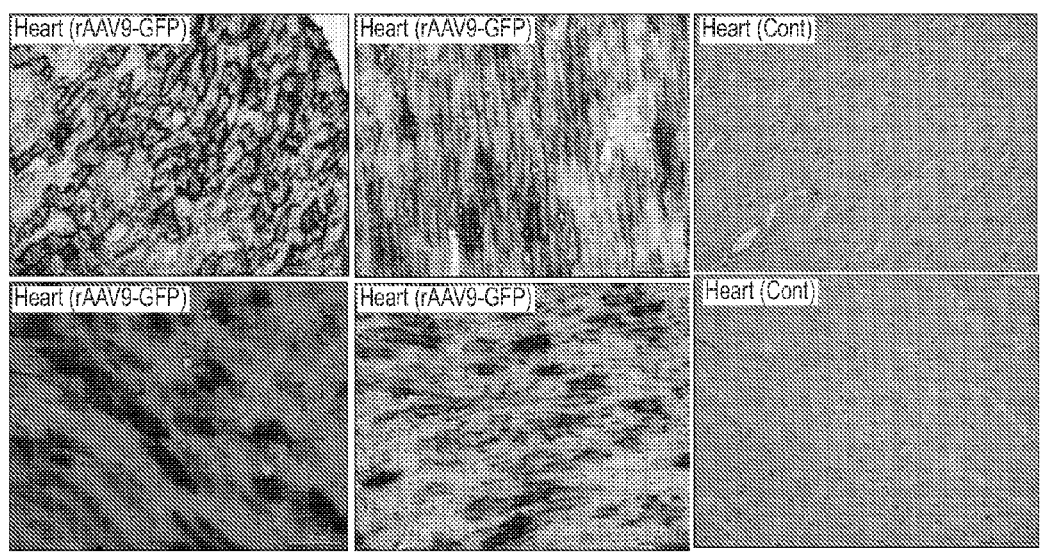
FIG. 2H is a pictorial diagram showing cardiac GFP expression one month after intravenous rAAV9-GFP injection. The four panels on the left (rAAV9-GFP) are shown with primary GFP antibody, while the two panels on the right (Cont) are shown without. The further data on AAV9 distribution demonstrates highest affinity of rAAV9-GFP expression for the heart. Liver and skeletal muscle showed low and the lungs only very faint expression.
Figure 21:
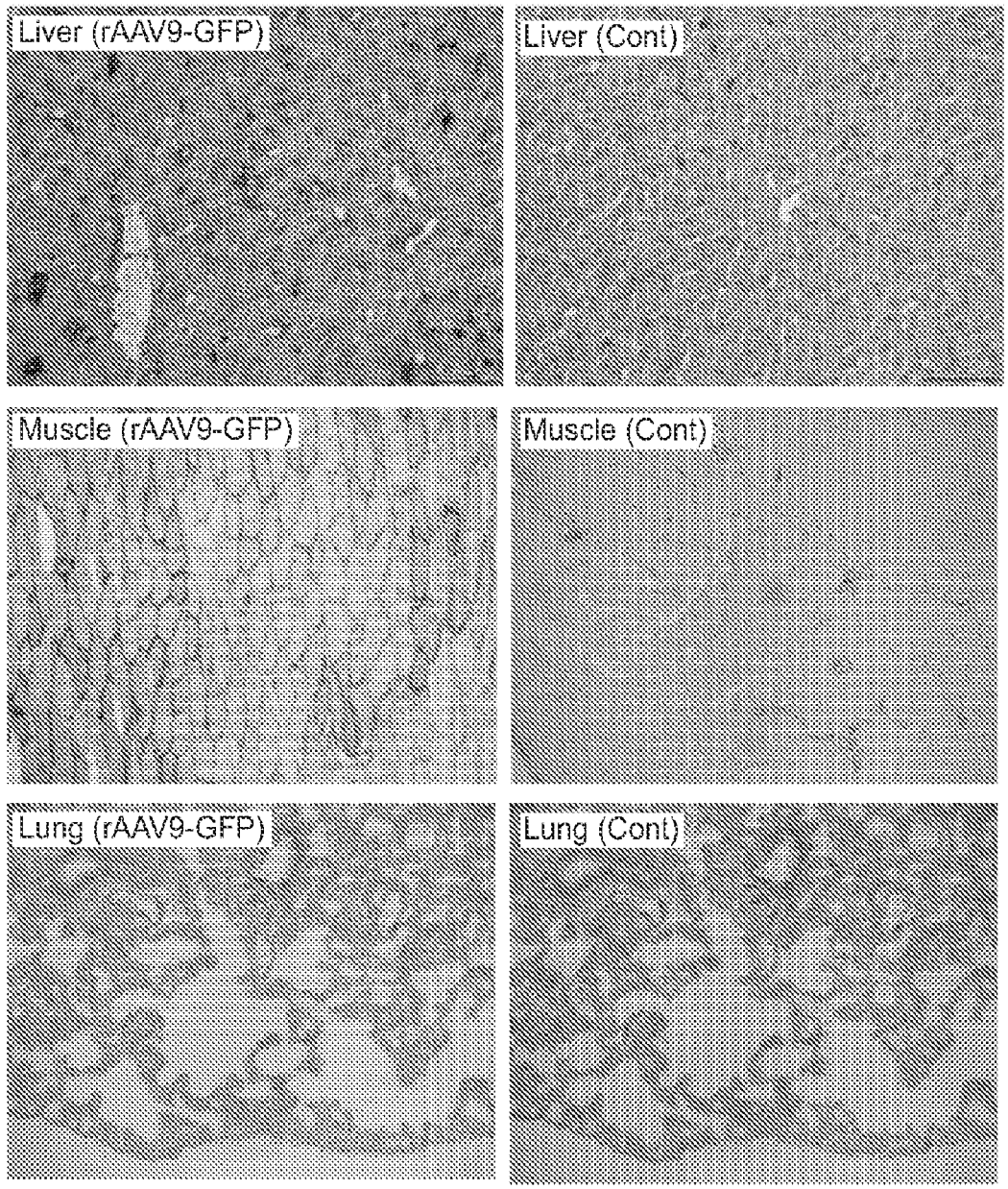

In addition to this visualization of GFP expression at the macroscopic scale, GFP immunhistochemical staining was performed one month after i.v. injection of rAAV9-GFP to evaluate its distribution at microscopic dimensions (FIGS. 2D, 2H and 2I). After blockade of endogenous peroxidase with 30% hydrogen peroxide, washing in PBS buffer, a polyclonal rabbit-anti-hrGFP antibody (VITALITY™, catalogue #240142, Stratagene) was added in 1:1000 dilution for 120 min. After washing, as secondary a polyclonal goat-anti-rabbit immunoglobulins/HRP antibody (catalogue #P0448, Dako, Glostrup, Denmark) was used in 1.50 dilution for 60 min. Staining and counterstaining with haemalaun was as described (Noutsias, et al. Human Coxsackie-Adenovirus-Receptor is Co-Localized with Integrins αvβ3 and αvβ5 on the Cardiomyocyte Sarcolemma and Upregulated in Dilated Cardiomyopathy—Implications for Cardiotropic Viral Infections. *Circulation*. 2001; 104:275-280).

For Western blot analysis of GFP expression in the different organs the polyclonal rabbit-anti-hrGFP antibody (VITALITY™, catalogue #240142 Stratagene) was used in 1:5000 dilution at 4° C. overnight. As secondary the polyclonal goat-anti-rabbit immunoglobulins/HRP antibody (catalogue #P0448, Dako, Glostrup, Denmark) was used in 1:2000 dilution at RT for 60 min. The GFP Western blots were then exposed to X-ray film for 5 min. Quantitation of these films is given in FIG. 2J.

Experimental Protocol for RNAi Therapy In Vivo

The adenoviral delivery system is well known in the art. Briefly, after anesthetizing the rats and performing a thoracotomy, a 22 G catheter containing 200 μl of adenoviral ($3 \times 10^{10}$ pfu) solution was advanced from the apex of the left ventricle to the aortic root. The aorta and main pulmonary artery were clamped for 40 sec distal to the site of the catheter and the solution injected, then the chest was closed and the animals were allowed to recover. For experiments with rAAV9, a simple tail vein injection was performed using $5 \times 10^{11}$ vector genomes of either rAAV9shRNA. Animals in the sham group were injected with saline.

Hemodynamics Evaluation During RNAi Therapy

Rats in the different treatment groups and at different stages following adenoviral gene transfer were anesthetized with 40 mg/kg of pentobarbital and mechanically ventilated. The chest was then opened through a mid-line incision and the heart exposed. A small incision was then made in the apex of the left ventricle and a 2.0 Fr. high fidelity pressure transducer (MILAR Instruments, TX) introduced into the left ventricle. Pressure measurements were digitized at 1 KHz and stored for further analysis. Left ventricular systolic pressure (LVSP), end-diastolic left ventricular pressure (LVDP), the maximal rates of pressure rise (+dP/dt) and of pressure fall (−dP/dt), and the time constant of relaxation (t) were measured or derived in the different groups. The time course of isovolumic relaxation was measured using the equation: $P=P_o e^{-t/\tau}+P_B$, where P is the left ventricular isovolumic pressure, $P_o$ is pressure at the time of peak −dP/dt and $P_B$ is residual pressure.

Histology of Hearts after RNAi Therapy

Cardiomyocyte size and cardiac fibrosis: Histological analyses were performed on a subset of animals to evaluate myocyte size (CMD) and collagen content (CAP). LV specimens were fixed with 10% formalin and embedded in paraffin. Sections (3 μm-thick) were stained with hematoxylin-eosin to determine CMD or with Azan-Mallory to assess CAP. In longitudinally oriented cardiomyocytes, transnuclear width was measured as CMD (FIG. 3F). Digital photographs were taken at six sites on each Azan-Mallory section. Interstitial/perivascular collagen area and myocyte area were determined separately by counting the computerized pixels using an NIH imager (FIG. 3E).

Statistical Analysis

Data are presented as mean±SD. Multiple comparisons were performed by ANOVA with STATVIEW (Abacus Concepts, Barkeley, Calif.). Statistical significance was accepted at the level of P<0.05. Two-factor ANOVA was performed to compare the different hemodynamic parameters among the different groups. For the echo data, where the variables were examined at various intervals, ANOVA with repeated measures was performed. Statistical significance was accepted at the level of p<0.05.

EXAMPLE 2

Optimization of RNAi Vector Systems

Figure 1D:
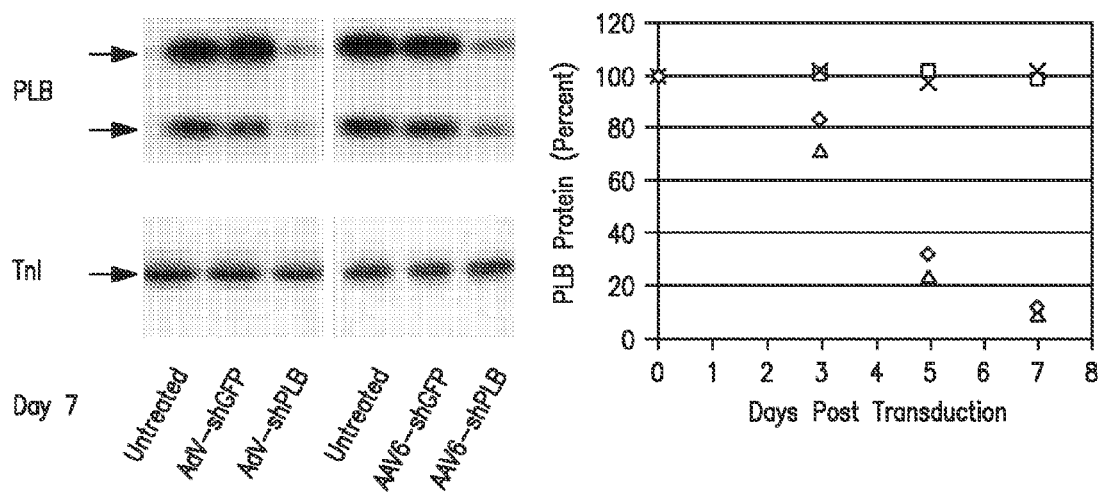
FIG. 1D is a pictorial and graphical diagraph showing on the left panels from a Western blot analysis of PLB protein during treatment of NRCMs, and on the right its quantitation on days 3, 5, and 7 after vector addition is shown. AdV-shPLB and rAAV6-shPLB resulted on day 7 in downregulation of cellular PLB to 9% and 13%, respectively, of baseline.
Figure 1E:
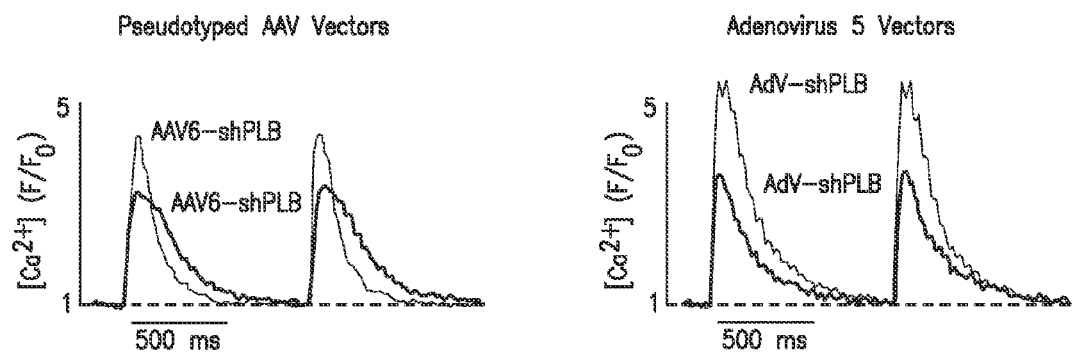
FIG. 1E is a graphical diagram showing that $[Ca^{2+}]_i$ transients in NRCMs during AAV9-shPLB treatment showed significantly higher amplitudes and accelerated transient kinetics (shortened TTP and τ) compared to the AAV9-shGFP group with transients indistinguishable from untreated cells. AdV-shPLB treatment also resulted in a significantly higher amplitude than in AdV-shGFP controls. In contrast to the AAV9 groups, TTP was prolonged in the AdV-shPLB vs. AdV-shGFP group which displayed no difference in τ.
Figure 1F:
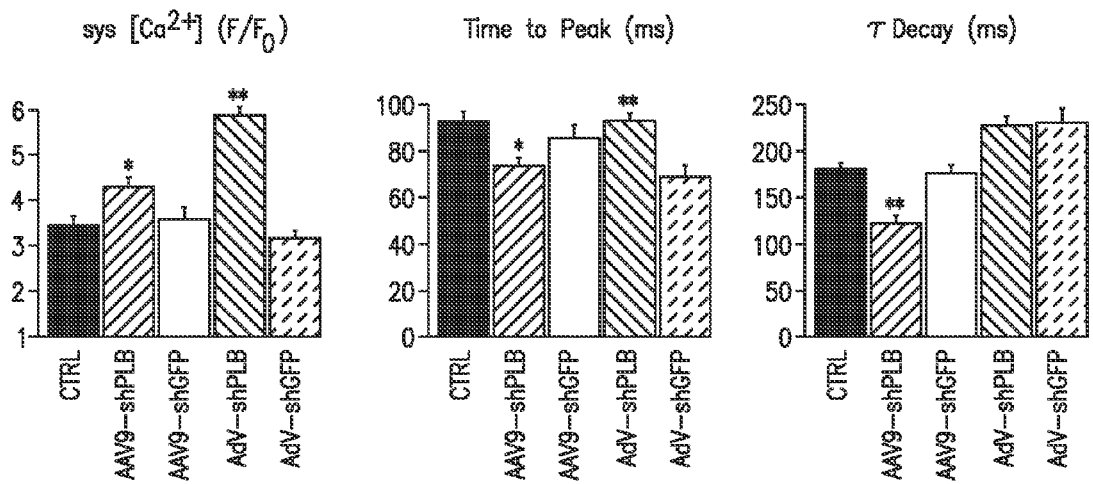
FIG. 1F is a graphical diagram showing a statistical evaluation of the $[Ca^{2+}]_i$ transients shown in FIG. 1E. * denotes $p<0.05$ and ** $p<0.01$.

The determinants of the silencing efficacy of viral RNAi vectors were investigated since it was observed that AAV-shPLB vectors with apparently minor structural differences showed grossly different shRNA production rates and target silencing in PNCMs in vitro (FIG. 1). For these initial studies in PNCMs the AAV2.6 pseudotype was used which has higher tranduction efficacy than AAV2.9 in vitro. For the later RNAi therapeutic investigations reported in FIGS. 2 and 3 only AAV2.9 was employed which displays superior cardiac transduction in vivo. The in vitro experiments showed that co-expression of a GFP marker protein to tag cells harboring the shPLB vector nearly abolished shPLB production (FIG. 1B) and PLB silencing (FIG. 1A). The presence of a CMV promoter in the expression cassette containing the U6 promotor used for shRNA transcription reduced shRNA production strongly if GFP was driven by the CMV, but also if CMV was linked to a β-intron (FIG. 5A). FIG. 1 shows that by far, the highest efficacy was displayed by an AAV construct previously considered too short for efficient packaging. Comparison of the shRNA transcription by AdV-shPLB vs AAV6-shPLB in PNCMs showed a decline to one third by day 10 for the adenoviral, but constant expression for the AAV vector (FIG. 1B). Ablation of PLB expression was >98% for both vectors at a dose of $4 \times 10^3$ p/c. Interestingly, incorporation of a CMV-GFP cassette to allow detection by in vivo imaging unexpectedly led to a vector unable to silence its target. CMV promoter-driven marker gene expression is apparently unsuitable for use in U6-shRNA vectors and only the most simple and efficient U6-shRNA vectors (FIG. 1) were selected for in vivo RNAi.

rAAV9-shRNA was employed for long-term therapy in vivo because of its highly stable shRNA production compared to AdV-shPLB and long-term stability in vivo. For short-term therapy the adenoviral vector was used. In vitro there was a lag of PLB ablation at the protein level compared to the mRNA level of several days, with protein leveling off at 9% (AdV-shPLB) and 12% (rAAV6-shPLB) of baseline, respectively, on day 7 (FIG. 1D). Measurement of $[Ca^{2+}]_i$ transients during AAV9-shPLB treatment of NRCMs (FIGS. 1E and 1F) showed that this vector led to significantly higher amplitude and accelerated transient kinetics (shortened TTP and $\tau$) compared to the AAV9-shGFP group with transients indistinguishable from untreated cells. AdV-shPLB treatment also resulted in a significantly higher amplitude compared to AdV-shGFP. In contrast to the AAV9 groups, TTP was prolonged in AdV-shPLB vs. AdV-shGFP and there was no difference in $\tau$. Studies of sarcoplasmic reticulum (SR) $Ca^{2+}$ loading in the AdV groups showed increased SR $Ca^{2+}$ loading and fractional $Ca^{2+}$ release (FR) from the SR in the AdV-shPLB vs. AdV-shGFP group (FIG. 5D). With respect to cell-to-cell variability of transduction in vitro, FIG. 5B shows grossly homogeneous GFP expression in NRCMs treated with rAAV-GFP marker vector which serves as best possible approximation to a direct demonstration of homogeneous shPLB expression in vitro. With current technology the latter cannot be visualized directly since coexpression of GFP together with shPLB extinguishes its silencing capacity (FIGS. 1B and 1C). Homogeneous spatial and temporal distribution of the RNAi vectors in rat hearts in vivo is also indirectly inferred by fluorescent imaging (FIGS. 2B and 2C) of a GFP vector of the same type (rAAV9) as used for RNAi therapy (FIGS. 3A-3D). FIGS. 2D and FIGS. 2H-2J show GFP immunohistochemical staining of the heart and other organs after i.v. injection of rAAV9-GFP. Strong and grossly homogenous expression in the heart contrasts with weak staining of liver and skeletal muscle and no visible staining of the lungs (for quantitation see FIG. 2J).

EXAMPLE 3

Efficacy of RNAi Therapy In Vivo

Transaortic constriction led to severe HF in rats after 30 weeks. The experimental protocol for in vivo RNAi therapy is outlined in FIG. 2. Fluorescent imaging and immunohistological analysis of a GFP vector of the same type (rAAV9) as used for the RNAi therapies showed grossly homogeneous cardiac GFP expression one month after i.v. injection at macroscopical and microscopical scale and may be assumed to approximate the cardiac shRNA expression levels generated by the RNAi vectors (FIGS. 2B-2D). Direct measurement of shPLB production in vivo is unfeasible with current technology. FIGS. 2F and 2G show significantly decreased cardiac PLB protein after treatment with either AdV-shPLB or rAAV9-shPLB. SERCA2a protein was decreased in failing hearts, whereas shPLB therapy was accompanied by an increase in cardiac SERCA2a protein. NCX was not significantly changed.

Treatment by aortic root injection of the AdV-shPLB as compared to the AdV-shGFP control vector (generating an shRNA sequence directed at GFP) served as a model of short-term treatment of severe HF. One month after injection diastolic function (FIG. 3A) was significantly ($p<0.05$) better in the AdV-shPLB than in the control group: left ventricular end-diastolic pressure (LVEDP) $10\pm3$ mmHg vs. $14\pm4$ mmHg, rate of LV pressure decrease (−dp/dt) $5215\pm540$ vs. $4017\pm471$ mmHg/sec, isovolumetric relaxation time constant Tau ($\tau$) $17\pm3$ vs. $24\pm4$ msec. Systolic function (FIG. 3B) was likewise improved with LV systolic pressure (LVSP) $90\pm5$ vs. $78\pm4$ mmHg, rate of LV pressure increase (+dp/dt) $7.448\pm659$ vs. $5.624\pm698$ mmHg/sec, and fractional shortening (FS) $46.1\pm3.2$ vs. $39.1\pm3.7\%$. Beyond the beneficial effects on hemodynamics, the large increase in LV weight and dilation after TAB were significantly reduced at one month: LV weight $1.34\pm0.22$ vs. $1.87\pm0.21$ g, LV/body weight (LV/BW) ratio $2.4\pm0.2$ vs. $3.2\pm0.2\times10^{-3}$, LV/tibial length (LV/TL) ratio $29.3\pm4$ vs. $43.3\pm5$ (FIG. 3C). These morphometric data post mortem correlated with echocardiography (FIG. 3D). Survival rates were 8/10 vs. 9/10.

Treatment by tail vein injection of the most efficient AAV9-shPLB as compared to the AAV9-shGFP vector served as a model of long-term therapy of chronic severe HF. Three months after injection, diastolic function (FIG. 3A) was significantly improved in the AAV9-shPLB therapy as compared to the control group and no longer significantly different from the sham-operated (no aortic banding) non-HF group: LVEDP was $8\pm3$ mmHg vs. $18\pm4$ (non-HF: $6\pm2$) mmHg, −dp/dt $5.722\pm503$ vs. $3.877\pm643$ (non-HF: $6.032\pm344$) mmHg/sec, Tau $16\pm3$ vs. $23\pm4$ (non-HF: $14\pm3$) msec. Systolic function (FIG. 3B) was also restored, although less so than the diastolic functional parameters: LVSP $92\pm4$ vs. $80\pm3$ (non-HF: $98\pm4$) mmHg, +dp/dt $7.851\pm803$ vs. $4.997\pm766$ (non-HF: $8.772\pm832$) mmHg/sec, and FS $50.1\pm2.1$ vs. $35.2\pm5.1\%$ (non-HF: $52.2\pm4.1$). Beyond hemodynamics this treatment reduced LV hypertrophy and dilation at 3 months: LV weight $1.34\pm0.12$ vs. $1.76\pm0.27$ g (non-HF: $1.11\pm0.09$), LV/BW $2.2\pm0.1$ vs. $3.1\pm0.2\times10^{-3}$ (non-HF: $1.8\pm0.2$), LV/TL $27.2\pm4$ vs. $45.3\pm5$ (non-HF: $24.5\pm4$) (FIG. 3C). Echocardiography corroborated reduction of LV wall thickness and dilation (FIG. 3D). Histology showed reduction of both cardiomyocyte size and cardiac collagen after 3 months of rAAV9-shRNA therapy (FIGS. 3E and 3F). Survival of AAV9-shPLB-treated animals after 3 months was 9/10 vs. 6/10 in the control group.

EXAMPLE 4

RNAi Therapy of Heart Failure

These data suggest that for intermediate time scales adenoviral vectors may suffice and even provide advantages over long-term stable AAV (Wang et al., *Nat Biotechnol* (2005) 23:321-328; Gregorevic et al., *Nature Medicine* (2004) 10:828-834; Inagaki et al., *Mol Ther* (2006) 14:45-53; Pacak et al., *Cir Res* (2006) 99:e3-9), since RNAi may be desirable only temporarily in acute and potentially reversible HF. In fact, the significant improvement of diastolic and systolic function and LV morphology one month after AdV-shPLB treatment is evidence of an at least functional therapeutic benefit from the adenoviral system. What has been previously shown for classical gene transfer therapy (del Monte et al., *Proc Natl Acad Sci USA* (2004) 101:5622-5627; Sakata et al., *J Mol Cell Cardiol* (2007) 42:852-861; Sakata et al., *Am J Physiol Heart Circ Physiol* (2007) 292:H1204-1207; Sakata et al., *Mol Ther* (2006) 13:387-996) may obviously work for RNAi-based strategies, too, although there are additional constraints for RNAi vector structure to avoid loss of therapeutic efficacy (FIGS. 1A and 1B) and disturbance of miRNA pathways.

Although shRNA production from AAVs is in several aspects different from classical gene transfer (FIG. 1), the data from the AAV arm of the present invention provide the first evidence that AAV-based shRNA production remains stable for several months at a level capable to improve cardiac function and possibly also survival. The AAV9 vector used here fulfils one first requirement for application in human HF, since it is cardiotropic in primates (Pacak et al., (2006)). In contrast to rodents, regulatable PLB modulation is most likely required in humans since permanent PLB deficiency or PLB dysfunction due to genomic mutations has been associated with cardiomyopathies (Schmitt et al., *Science* (2003) 299:1410-1413; Haghighi et al., *Proc Natl Acad Sci USA* (2006) 103:1388-1393; Zhao et al., (2006) 113:995-1004). Drug-regulatable RNAi appears possible, however, on current vector platforms.

After RNAi therapy SERCA2a expression was found to be increased compared to HF groups, consistent with the fact that RNAi therapy normalized LV function. Since SERCA2a expression is a well known marker of the degree of HF, its increase following RNAi therapy by shPLB reflects the improved status of cardiac function.

EXAMPLE 5

Cardiomyocyte microRNA Expression During RNAi Therapy

The cellular machinery of RNAi evolved over millions of years and is the most efficient and versatile mechanism known for specific gene silencing. shRNAs exploit this machinery to mediate therapeutic effects by mimicking the endogenous process, achieve silencing at far lower concentrations than antisense RNAs, but may disturb cellular miRNA pathways (Grimm et al., *Nature* (2006) 441:537-541). Since miRs play important roles in cardiac morphogenesis (Zhao et al., *Cell* (2007) 129:303-317), hypertrophy (Care et al., *Nature Medicine* (2007) 13:613-618; van Rooij et al., *Science* (2007) 316:575-579), arrhythmogenesis (Yang et al., *Nature Medicine* (2007) 13:486-491), and failure (Thum et al., *Circulation* (2007) 116:258-267; van Rooij et al., *Proc Natl Acad Sci USA* (2006) 103:18255-18260) possible side-effects of the RNAi vectors were searched for at the miRNA level in PNCMs/NRCMs. First, under standard culture conditions and then in the presence of the hypertrophy-inducing drug phenylephrine (PE). In the absence of this hypertrophic stimulus none of the vectors used in vivo had any significant effect on the cellular miRs 1, 21, 133a, 195, 208 with known functional significance in the heart (FIG. 4B). In the presence of PE there was a marked reduction of several cardiomyocyte miRNAs on day 5 of culture (FIG. 4A). Remarkably, this decline in the levels of miRNAs with antihypertrophic (Care, et al. (2007) MicroRNA-133 controls cardiac hypertrophy. *Nat Med* 13, 613-8; and van Rooij, et al. (2007) Control of stress-dependent cardiac growth and gene expression by a MicroRNA. *Science* 316, 575-9) and anti-arrhythmogenic (Yang, et al. (2007) The muscle-specific microRNA miR-1 regulates cardiac arrhythmogenic potential by targetic GJA1 and KCNJ2. *Nat Med* 13, 486-191) potential was reversed in PNCMs treated with AdV-shPLB or AAV6-shPLB which restored these miRNA levels to base line.

Figure 2J:
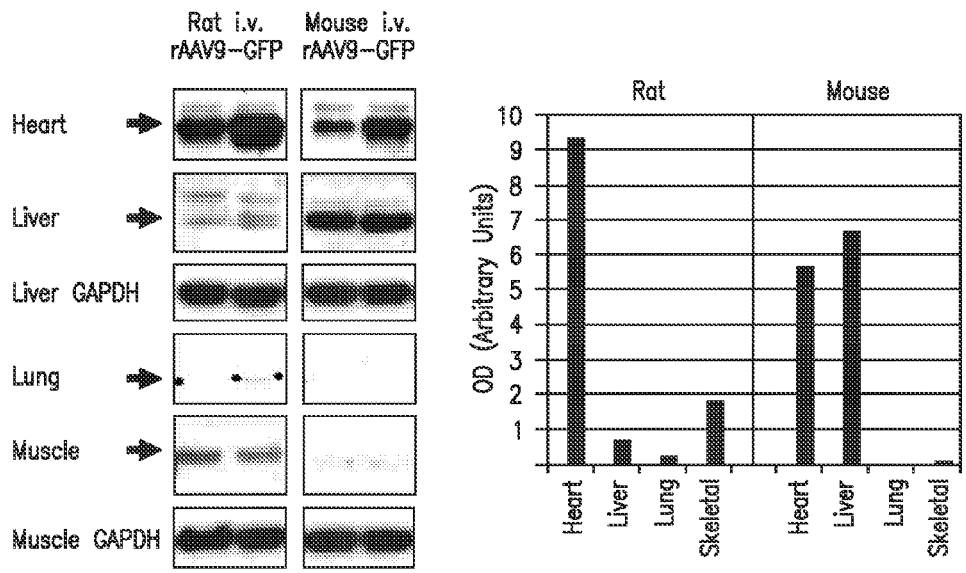
FIG. 2J is a pictorical and graphical diagram showing GFP quantitation by immunoblot in different organs after intravenous rAAV9-GFP injection.

In the presence of PE there was a marked reduction of cardiomyocyte miRs on day 5 of culture (FIG. 4B). Remarkably, this decline of miRs with anti-hypertrophic (Zhao et al., (2007); Care et al., (2007)) and anti-arrhythmogenic (Yang et al., (2007)) potential was reversed in PNCMs treated with AdV-shPLB or AAV6-shPLB which restored these miRNA levels to baseline, of particular interest are miRNA-133 and miRNA-1. Since malignant arrhythmias are important complications in HF, deregulation of any arrhythmia-related microRNA such as miRNA-1 (Yang et al., (2007)) by a novel treatment should be considered as possibly serious adverse effect. However, the in vitro data show that the PE-induced reduction in miRNA-1 was counteracted by shPLB treatment (FIG. 4A-4C). In conjunction with the trend towards improved survival in the AAV-shPLN treatment group there is thus so far no evidence of arrhythmogenic side-effects of this therapy. Rat hearts treated with shPLB vector had higher miRNA levels than the shGFP group (FIGS. 2H-2J). With respect to possible side-effects of the RNAi vectors, HE stains of the liver (FIG. 2E) and other organs after vector injection revealed no pathological findings.

miRNA-133 plays a critical role in controlling cardiomyocyte size (Care et al., (2007)) and is of interest with respect to the hypertrophy-reduction by the RNAi therapy. Irrespective of the molecular mechanism by which miRNA-133 levels are restored by the shPLB treatment in vitro, their elevation must by assumed to have an anti-hypertrophic effect. Whereas improved systolic and diastolic function during RNAi therapy results immediately from its influence on excitation-contraction coupling (ECC) via the global $Ca^{2+}$ transients, the marked reduction of LV hypertrophy and dilation observed (FIGS. 3C, 3D and 3F) is not as easily deduced, since the RNAi therapy targets primarily a single component of global $Ca^{2+}$ cycling only. Unexpectedly, this narrowly targeted intervention nevertheless restored several PE-induced miRNA suppressions to normal levels (FIG. 4A). Since in vitro, neither hemodynamic stress, nor neurohumoral of cytokine activation as in HF in vivo can play any role, this restoration apparently results from $Ca^{2+}$ homeostasis modulation at the cellular level. Since one cannot assume a direct effect of the PLB ablation on cellular miRNAs, the RNAi-induced changes in $Ca^{2+}$ homeostasis apparently affect not only the contraction-related global $Ca^{2+}$ transients, but also separate and insulated $Ca^{2+}$ signals generated in the perinuclear space (Wu et al., *J Clin Invest* (2006) 116:675-682; Molkentin J., *J Clin Invest* (2006) 116:623-626) which determine transcriptional changes as during hypertrophy. The miRNA suppressions induced by PE and corrected by RNAi could merely reflect indirect changes in the regulatory network of the cell resulting from altered $Ca^{2+}$ homeostasis. Alternatively, the latter could directly influence miRNA expression as a primary target.

Based on these results, a highly efficacious localized RNAi therapeutic strategy has been developed for cardiac disease. When using optimized RNAi vectors and aortic root vector injection to confine RNAi to the heart, there was no evidence of toxicity or disturbed miRNA pathways. While not being bound by theory, correction of hypertrophy-associated miRNA deregulations by the vectors miRNA suggests miRNA involvement in the therapeutic process. While short-term RNAi-mediated PLB silencing by an adenovector improved cardiac function after 1 month, long-term RNAi from an optimized cardiotropic AAV9 vector improved function, morphology, and survival in HF rats over a period of 3 months.

Further, use of the disclosed vectors results in decreased ventricular arrythmias in models of ischemia perfusion, as well as improvement in ventricular function. Moreover, inhibition of PLB increases survival in animals with pressure overload hypertrophy in transition to heart failure.

Although the invention has been described with reference to the above examples, it will be understood that modifications and variations are encompassed within the spirit and scope of the invention. Accordingly, the invention is limited only by the following claims.

What is claimed is:

1. An adeno-associated virus (AAV) vector comprising at least one AAV terminal repeat, wherein the vector comprises an RNAi expression cassette comprising a nucleotide sequence set forth in SEQ ID NO:1, whose RNAi expression product leads to a decrease in expression of phospholamban (PLB) mRNA or PLB activity.

2. The AAV vector of claim 1, wherein the AAV is serotype 9.

3. A method of treating heart failure in a subject comprising administering to a subject in need thereof the AAV vector of claim 1 in an amount effective to treat heart failure of the subject.

4. The method of claim 3, wherein the AAV is serotype 9.

5. The method of claim 3, wherein expression of PLB mRNA is inhibited.

6. A method of increasing calcium uptake into the sarcoplasmic reticulum (SR) comprising contacting a muscle tissue sample with the adeno-associated virus (AAV) vector of claim 1, thereby increasing calcium uptake in the SR.

7. The method of claim 6, wherein the RNAi comprises a nucleotide sequence that hybridizes under stringent conditions to a nucleotide sequence of a PLB target gene mRNA, thereby enhancing contractility of cardiomyocytes as compared to contractility prior to contact with the vector.

8. The method of claim 6, wherein expression of the RNA coding region of the RNAi expression cassette results in the down-regulation of the expression of the PLB gene.

9. The method of claim 6, wherein PLB gene expression is inhibited by at least 10%.

10. The method of claim 6, wherein the AAV genome is self-complementary.

11. The method of claim 6, wherein the AAV is serotype 9.

* * * * *

SEQUENCE LISTING

<160> NUMBER OF SEQ ID NOS: 2

<210> SEQ ID NO 1
<211> LENGTH: 71
<212> TYPE: DNA
<213> ORGANISM: Artificial Sequence
<220> FEATURE:
<223> OTHER INFORMATION: Synthetic construct

<400> SEQUENCE: 1
ggatcccgta ccttactcgc tcggctattc aagagatagc cgagcgagta aggtattttt    60
tggaaaagct t                                                         71

<210> SEQ ID NO 2
<211> LENGTH: 19
<212> TYPE: RNA
<213> ORGANISM: Artificial Sequence
<220> FEATURE:
<223> OTHER INFORMATION: Synthetic construct

<400> SEQUENCE: 2
uaccuuacuc gcucggcua                                                 19